(12) United States Patent
Nordlund et al.

(10) Patent No.: US 7,718,381 B2
(45) Date of Patent: May 18, 2010

(54) METHOD OF SCREENING FOR CELL COLONIES THAT EXPRESS A SOLUBLE VARIANT OF A TARGET PROTEIN

(75) Inventors: Pär Nordlund, Roslagsgatan 47, Stockholm (SE) S-113 54; Tobias Cornvik, Fyrskeppsvägen 118 2 Tr, Johaneshov (SE) S-121 54; Sue-Li Dahlroth, Johaneshov (SE); Rose-Marie Knaust, Gauting (DE)

(73) Assignees: Par Nordlund, Stockholm (SE); Tobias Cornvik, Stockholm (SE)

( * ) Notice: Subject to any disclaimer, the term of this patent is extended or adjusted under 35 U.S.C. 154(b) by 520 days.

(21) Appl. No.: 10/562,734

(22) PCT Filed: May 27, 2004

(86) PCT No.: PCT/GB2004/002271
§ 371 (c)(1),
(2), (4) Date: Jul. 7, 2006

(87) PCT Pub. No.: WO2005/003784
PCT Pub. Date: Jan. 13, 2005

(65) Prior Publication Data
US 2007/0087325 A1  Apr. 19, 2007

(30) Foreign Application Priority Data
Jul. 2, 2003  (GB) ................ 0315525.6

(51) Int. Cl.
G01N 33/68 (2006.01)
G01N 33/53 (2006.01)
G01N 33/569 (2006.01)

(52) U.S. Cl. ............... 435/7.2; 435/4; 435/7.1; 435/7.32

(58) Field of Classification Search .............. None
See application file for complete search history.

(56) References Cited

U.S. PATENT DOCUMENTS 5,506,121 A * 4/1996 Skerra et al. ............ 435/69.7

2002/0127587 A1   9/2002  Simms et al.

FOREIGN PATENT DOCUMENTS

GB      2152214 A      7/1985

OTHER PUBLICATIONS

Heinis, Christian, et al., "Two General Methods for the Isolation of Enzyme Activities by Colony Filter Screening," *Chemistry & Biology*, Mar. 2002, pp. 383-390, vol. 9.
Knaust, Rosemarie K.C., et al., "Screening for Soluble Expression of Recombinant Proteins in a 96-Well Format," *Analytical Biochemistry*, 2001, pp. 79-85, vol. 297.
Maxwell, Karen L., et al., "A simple in vivo assay for increased protein solubility," *Protein Science*, 1999, pp. 1908-1911, vol. 8.
Peabody, David S., et al., "Isolation of viral coat protein mutants with altered assembly and aggregation properties," *Nucleic Acids Research*, 2001, pp. 1-7, vol. 29, No. 22 e113.
Skerra, Arne, et al., "Filter Screening of Antibody Fab Fragments Secreted from Individual Bacterial Colonies: Specific Detection of Antigen Binding with Two-Membrane System," *Analytical Biochemistry*, 1991, pp. 151-155, vol. 196.
Voss, Selma et al., "Mutagenesis of a flexible loop in streptavidin leads to higher affinity for the *Strep*-tag II peptide and improved performance in recombinant protein purification," *Protein Engineering*, 1997, pp. 975-982, vol. 10, No. 8.
Waldo, Geoffrey S., "Genetic screens and directed evolution for protein solubility," *Current Opinion in Chemical Biology*, Feb. 2003, pp. 33-38, vol. 7, No. 1.
Waldo, Geoffrey S., et al., "Rapid protein-folding assay using green fluorescent protein," *Nature Biotechnology*, Jul. 1999, pp. 691-695, vol. 17.
Yang, Jin Kuk, et al., "Directed evolution approach to a structural genomics project: Rv2002 from *Mycobacterium tuberculosis*," *PNAS*, Jan. 21, 2003, pp. 455-460, vol. 100, No. 2.

* cited by examiner

*Primary Examiner*—Vera Afremova
(74) *Attorney, Agent, or Firm*—Rothwell, Figg, Ernst & Manbeck

(57) ABSTRACT

The present invention concerns a method of identifying a cell colony which expresses a soluble variant of a target protein which method comprises (a) subjecting the cell colony to conditions which are capable of causing lysis thereof; (b) filtering the lysate through a filter having pores which allow only soluble proteins to pass through the filter; and (c) detecting target protein which has passed through the filter where the target is not detected an the basis of its own enzymatic activity. The invention further covers the identification of a cell colony expressing a soluble variant of a membrane protein using steps (a) and (b) of the method above. A kit for use in the methods is also covered by the invention.

14 Claims, 18 Drawing Sheets

| | His | | CoFi-Blot | | Flag | |
|---|---|---|---|---|---|---|
| A | High | High | Low | High | High | No |
| B | High | Low | High | High | No | No |
| C | High | No | No | Medium | Medium | No |
| D | No | Medium | Medium | Low | Medium | High |
| E | Medium | No | Medium | Medium | High | No |
| F | Low | No | Medium | High | High | High |
| G | High | Medium | No | High | Low | No |
| H | Low | No | No | Low | No | No |

(ii)

Legend:
- False Positive or Negative
- Predicted as soluble but in the most distant category
- Predicted as soluble but in a neighbouring category
- Correctly predicted in the right category

FIG. 4b CONT'D (ii)

| | | Centrifugation | | | Flag | |
|---|---|---|---|---|---|---|
| | | His | | | | |
| A | High | High | No | High | High | No |
| B | Low | Medium | High | Medium | No | No |
| C | Low | No | No | Medium | Medium | No |
| D | Medium | Medium | Medium | Medium | Low | High |
| E | Medium | No | No | Medium | High | High |
| F | Low | No | High | Medium | High | Low |
| G | High | High | No | High | Low | No |
| H | No | No | No | Low | No | No |

FIG. 4b CONT'D

RORA 5-8 minutes
(~100-190 aa:s)

RORA 20-24 minutes
(~450-560 aa:s)

SOCS-2 1-4 minutes
(~0-90 aa:s)

SOCS-2 9-12 minutes
(~210-300 aa:s)

Colony screen of a RORa library. The positive controls (➡) are added to the plate with the library to facilitate orientation. ➤ Indicates examples of colonies judged to produce soluble protein.

Colony FiDo with reference

5:2500 Colonies

METHOD OF SCREENING FOR CELL COLONIES THAT EXPRESS A SOLUBLE VARIANT OF A TARGET PROTEIN

The invention relates to a method of screening protein molecules, in particular to methods for identifying soluble proteins and for detecting colonies expressing a soluble target protein.

The production of pure or semi-pure proteins is important in many commercial and academic research and development programs. Often such proteins are produced recombinantly. Recombinant proteins can constitute products (e.g. enzymes for use in biomedical assays or in industrial processes) and are also used in the process of developing pharmaceutical drugs. In pharmaceutical drug development processes, these proteins are often used for structural studies (where methods such as NMR and x-ray crystallography are employed), and in biochemical or biophysical studies of the target protein. In academic research, recombinantly expressed proteins are used for biochemical, biophysical and structural characterisation. Additionally, the sequencing of the human genome has now revealed many potential targets for recombinant expression to elucidate the function of gene products.

Traditionally, recombinant proteins are produced by the overexpression of a gene of interest. However, many proteins aggregate (e.g. in inclusion bodies) when overexpressed and fail to fold into their native conformation. Such protein aggregates must be dissolved and correctly refolded before they can be used in many of the above methods. However refolding proteins from inclusion bodies usually results in very low yields of proteins and often it is not possible to determine if the protein isolated is in fact correctly folded.

To improve the yields of proteins obtained, it is therefore important for proteins to have a high solubility. Several studies have now shown that protein solubility may be substantially increased by amino acid substitutions at particular positions. Mutant libraries of target proteins have been created in order to select those which have increased solubility and hence are capable of being highly expressed. Indeed, proteins which are naturally insoluble, may be mutated and expressed in soluble form. The process of mutating proteins for isolating/detecting soluble variants is known in the art as directed evolution. Several methods of mutagenesis are available including site directed mutagenesis, truncation of the sequence ends, use of an exonuclease enzyme and introduction of a randomised cassette of nucleotides into the nucleic acid sequence.

Mutant libraries of proteins must further be screened to detect the recombinant clone(s) containing soluble variants. Several screening methods have been described, which select proteins with increased solubility. Maxwell et al. (Protein Science, 1999, 8, 1908-1911), described a simple assay for assessing solubility using chloramphenicol acetyltransferase (CAT) fusion proteins, this was based on the principle that cells expressing fusions of an insoluble protein to CAT exhibit decreased resistance to chloroamphenicol compared to fusions with soluble proteins. Experiments were carried out using the wild-type (insoluble) catalytical core domain of HIV integrase and a soluble variant with amino acid substitutions at positions F185. Selection experiments on a library of proteins were not carried out using this screen, and the authors hypothesise that a large number of false positives could arise. Hence, it is clear that more reliable screens for soluble proteins are required.

Another group, Waldo et al. (Nature Biotechnology, 1999, 17, 691-695), have developed a soluble protein screen using proteins with N-terminal fusions to green fluorescent protein (GFP). Waldo et al. demonstrated that the correct folding of the GFP protein domain (and hence its ability to fluoresce) is directly related to the folding robustness and avoidance of inclusion body formation of the protein of interest.

The correlation reported between non-fusion solubility and GFP fusion fluorescence has however been reported as not perfect, where solubility can be both over and under estimated. Generally, it will be recognised that techniques which rely on the properties of a protein fused to a reporter moiety will not always give a good indication of how the target protein free of its fusion partner will behave.

Peabody and Al-Bitar (Nucleic Acids Research, 2001, 29, No. 22 e113 1-7) developed a soluble protein screen, wherein recombinant bacterial colonies were overlayed with agarose gel. Proteins diffused from the colonies through the overlayed gel depending on molecular weight. Soluble variants which diffused faster gave larger diameter spots of greater intensity than insoluble variants. Diffusion takes 24 hours and so this method is not suitable for high throughput screening.

In Knaust and Nordlund (Analytical Biochemistry, 2001, 297, 79-85), a screen for soluble proteins was developed using filtration of cells lysed in culture in 96 well plates. Recombinant bacteria were grown on agar plates and then used to inoculate media in 96 well plates. The cultures were grown, lysed and filtered. Soluble proteins pass through a filter into a microtiter plate, positive recombinant bacteria were identified by screening the filtrates by Western blot.

Although this method proved to be reliable for soluble protein detection, it was also time consuming to process large numbers of recombinant clones due to the many pipetting steps necessary.

The present inventors have now developed a screening method which can process large numbers of recombinant bacteria in a short period of time. Surprisingly, it has been found that lysis of cells and filtration of lysates can be carried out directly on colonies of cells, hence eliminating the requirement to grow colonies in culture and the multiple pipetting steps involved with this technique.

The present invention is hence capable of operating on large numbers of variants, is inexpensive and has a high reliability of predicting soluble variants.

Thus in one aspect the present invention provides a method of treating one or more colonies of cells which method comprises:

(a) subjecting the cell colonies to conditions which are capable of causing lysis thereof; and (b) filtering the lysate of step (a) through a filter having pores which allow only soluble proteins to pass through the filter.

The invention provides a method of detecting one or more colonies expressing a soluble target protein, where the selection occurs on the basis of the ability of the protein of interest to pass through the filter.

The invention particularly covers methods wherein the target protein is a membrane protein. A membrane protein is one which is associated with one of the membranes of a cell, and can either be found within the membrane or bound to it. The membrane may be an intracellular membrane or the outer cell membrane. Preferably the membrane is an intracellular membrane, and most preferably is an intracellular membrane of *E. coli*.

The methods of the invention detect soluble proteins and colonies expressing soluble variants of a given protein. Membrane proteins are generally considered insoluble and therefore the target membrane proteins will be those which are capable of being made soluble, conveniently this solubilising may be achieved by subjecting the protein to mutagenesis, e.g. as described in Example 4.

The invention also covers a method of selecting one or more colonies expressing a soluble non-enzymatic target protein. 'Non-enzymatic' proteins are proteins which do not themselves possess enzymatic activity and are not capable of catalysing a biochemical reaction. 'Non-enzymatic' target proteins can be fused to other proteins e.g. tags such as horseradish peroxidase which do have enzymatic activity.

Preferably this method is used as a screening method to identify colonies expressing soluble proteins. The filter through which the proteins pass acts as the screen, i.e. the identification of colonies expressing soluble proteins occurs as a direct result of whether or not the target protein has passed through the filter.

Thus, the present invention also provides a method of determining whether or not a cell colony expresses a soluble variant of a target protein which method comprises:

(a) subjecting said cell colony to conditions which are capable of causing lysis thereof;

(b) filtering the lysate of step (a) through a filter having pores which allow only soluble proteins to pass through the filter; and (c) detecting target protein which has passed through the filter.

In step (c) the target protein is detected and the presence of target protein indicates that the corresponding cell colony produces a soluble variant of that target protein. Preferably, the target protein is not detected on the basis of its own enzymatic activity. However, detection can occur on the basis of the enzymatic activity of a tag fused to the target protein of interest, e.g. horseradish peroxidase, G-S-T or luciferase. Moreover, the tag may participate as a substrate in an enzymatic detection method, His tags being particularly suitable in this regard. For example, INDIA His Probe-HRP (Pierre, Rockford Ill., USA) can be used for detection wherein the target protein of protein of interest is either poly-histidine tagged or is histidine rich and where the target protein is detected by a Nickel activated derivative of horse radish peroxidase which binds to His tags. Alternatively, a non-enzymatic (i.e. non-catalytic) detection method is used, (i.e. no method based on substrate conversion).

Preferably detection is based on affinity binding between the target protein and a detection moiety, for example an antibody or antibody fragment or affibody (non Ab based protein binding partner). Such methods allow for rapid and reliable analysis of a wide variety of target molecules, including those which themselves possess no catalytic activity.

Alternatively viewed, the present invention provides a method of identifying a cell colony which expresses a soluble variant of a target protein, which method comprises:

(a) subjecting said cell colony to conditions which are capable of causing lysis thereof;

(b) filtering the lysate of step (a) through a filter having pores which allow only soluble proteins to pass through the filter; and (c) detecting target protein which has passed through the filter, wherein the target is not detected on the basis of its own enzymatic activity.

As discussed below, the proteins in the filtrate are localised on a solid support, e.g. a capture membrane, and therefore it is a simple matter to correlate target proteins identified in the filtrate with individual cell colonies when more than one cell colony is analysed at the same time. Typically 50 or more, 200 or more or even 1000 to 2000 or more colonies are analysed simultaneously.

As used herein, the term "colony" or "colonies" describes a circumscribed group of cells, normally derived from a single cell or small cluster of cells, growing on a solid or semi-solid medium. Colonies can be formed from any cell type which can be made to express recombinant proteins and which can grow on solid or semi solid media. For example, colonies can be formed of prokaryotic e.g. bacteria or eukaryotic cells e.g. yeast, unicellular eukaryotes such as *Leishmania*, insect cells or mammalian cells or cell lines. Preferably colonies are formed of *E. coli, Bacillus subtilis, Streptococcus lactis, Streptomyces lividens, Lactococcus lactis, Staphylococcus aureas, Aspergillus niger, Picia pastoris, Saccharomyces cerevisiae* or *Schizosaccharomyces pombe*.

Semi-solid or solid media used to grow colonies typically consists of culture media with the addition of 0.1% or greater agar. More preferably, solid or semi-solid media contains at least 0.2%, e.g. at least 1.0% or at least 1.5% agar. "Colonies" do not encompass cells grown in liquid culture.

The lysis step of the present invention can be carried out chemically or otherwise using reagents which are well known in the art e.g. urea, lysozyme containing buffers or detergents. The degree of lysis must be sufficient to allow the proteins of the cell to pass freely out of the cell. Typically, when dealing with membrane bound proteins, lysis is performed in the presence of detergents or amphiphiles, for example Triton X-100 or dodecylmaltoside, to release the protein from the membrane. Preferably, the lysis step is non-denaturing, allowing proteins to retain a native, i.e. correctly folded or native-like conformation, this is referred to herein as 'native lysis'. The lysis step can alternatively be carried out by freeze thawing the colonies. More preferably, lysis is carried out using both native lysis buffer and freeze thawing the colonies. Preferably, the native lysis buffer contains lysozyme, for example at 50-750 µg/ml, more preferably at 100-200 µg/ml. DNAse can also be found in native lysis buffer preferably at 250-750 µg/ml. Native lysis buffer may contain, for example 20 mM Tris, pH 8, 100 mM NaCl, lysozyme (200 µg/ml) and DNAse I (750 µg/ml).

Typically, the colonies will be exposed to the lysis mixture (buffer) for 15-60 minutes, preferably around 30 minutes. The step of freeze thawing is preferably repeated, i.e. two or more cycles, preferably 3 or more cycles of freeze thawing are performed. In one preferred embodiment lysis is achieved by a 30 minute incubation at room temperature with lysis buffer and three x 10 minutes freeze thawing.

Typically, the percentage of cells lysed within a colony during the lysis step is 5-50%. Colonies to be lysed preferably contain at least $10^4$ cells e.g. at least $10^5$, at least $10^6$, at least $10^7$ or at least $10^8$ cells. The size of such colonies is typically 0.1-3 mm$^2$, preferably 0.2-2 mm$^2$ and more preferably 0.25-1 mm$^2$. However, it will be appreciated that the present method could be used to screen a wide range of colony sizes.

A "native-like" protein or "native" protein refers to a soluble intracellular, extracellular or membrane protein wherein the protein exhibits a native-like conformation and functions similarly or identically to the naturally occurring protein. "Native" or "native-like" proteins are expressed in soluble form and/or are correctly folded. Native-like membrane proteins do not have to be present free in solution, but may be present in membrane vesicles rather than inclusion bodies. Thus "native-like" proteins are generally not insoluble, present in inclusion bodies, aggregated or misfolded. According to the methods of the present invention, it is the soluble proteins which are able to pass through the filter and thus be separated from insoluble proteins. As described herein, this allows the identification of colonies expressing soluble proteins, e.g. through the use of blotting techniques.

The correlation between solubility and correct, i.e. native or native-like folding means that the method is able to separate proteins with their native conformation from misfolded/aggregated proteins.

A "soluble" protein can thus be defined with reference to possession of a native or native-like conformation. Further, a soluble protein can be described as a protein which remains in the supernatant after cell lysis and centrifugation thereof. Centrifugation can be carried out at least 1000 g, preferably at least 3000 g, preferably at least 10000 g and more preferably at around 20000 g. Centrifugation can be carried out at 100000 g. The duration of centrifugation can be from 1 minute (typically at least 10 mins) to at least 1 hour, where the duration required generally decreases as the centrifugal force increases. Particularly suitable conditions for providing only soluble proteins in the resultant supernatant include 10 minutes at 100000 g, 30 minutes at 3000 g or 15 minutes at 20000 g. 15 minutes at 20000 g as described in the Examples being especially suitable.

Some proteins which pass through the filter will not correspond exactly to any naturally occurring protein. For example a library of proteins may be generated based on a target protein in order to identify related mutants with improved solubility in a given expression system compared to a problematic target protein. In these circumstances it is appropriate to consider the soluble mutants as having a "native-like" conformation.

The filtration step of the invention can be carried out using standard filter membranes for the filtering of biological samples. The filters will typically have a pore size from 0.015 µm to 12 µm, preferably from 0.35 to 1.2 µm, preferably from 0.45 to 1.2 µm, more preferably from 0.45 to 0.8 µm. Preferably, the filters have pore sizes below 4.0 µm, typically below 2.0 µm, more preferably below 1.0 µm. For several cell types, in particular bacteria e.g. *E. coli*, an optimal pore size may be 0.1-1.5 µm. For eukaryotic cells, preferred pore sizes may be larger. It will be appreciated that filters are manufactured and marketed as having a particular pore size but the manufacturing process may occasionally result in a few smaller or larger pores; the sizes listed, which refer to the diameter, are thus the most common pore size of a given filter. Although reference is made to a range of potential pore sizes, any single filter will usually have one designated pore size, e.g. 0.45 µm. Suitable filters are Super and GH polypro (from Pall) and Nucleopore (from Whatman).

It will be appreciated that different cell types may require the use of filters with different pore sizes, due for example to their different tendencies to harbour aggregated proteins, which aggregates may also have varying properties in different cell types. Selection of a suitable filter is well within the competency of someone skilled in this field. For example, it is possible to select an appropriate pore size, by using a set of test proteins for the desired cell type and investigating their behaviour with filters of varying pore sizes. Such data should then be compared with centrifugation data as shown in Example 1.

Preferably the filter is overlayed on the colonies to lift the colonies/protein from the semi-solid or solid growth media (FIG. 1). Alternatively, filters could be placed on the growth media and cells seeded directly onto the filter, the filter could then simply be lifted off with the colonies already on it. Preferably, the lifting of colonies from their growth media can be carried out prior to the lysis step. The lysis can hence be carried out directly on colonies on a filter. The filter with colonies attached can be treated with lysis buffer (FIG. 2) or overlayed on other membranes/filters treated with lysis buffer Filtration is carried out after lysis, i.e. it is the lysate which is filtered. It will be appreciated however that filtration and lysis may occur simultaneously when considering a whole colony since some cells may undergo lysis before others and hence may be filtered before or at the same time as others are lysed. Preferably, proteins which pass through the filter are held on a solid support, e.g. a capture membrane, to allow screening/detection of any proteins of interest and then to allow the identification of colonies expressing such proteins. Such capture membranes may typically comprise nitrocellulose. Preferably, the detection of the target protein is not on the basis of its own enzymatic activity. Detection can however occur on the basis of the enzymatic activity of a tag fused to the target protein or where the tag acts as a substrate in an enzymatic detection method. It will be appreciated however that the first filter which separates soluble from insoluble proteins acts as the essential screen for this invention. In a preferred embodiment, proteins can simply be allowed to pass through the filter, possibly as a result of an active capillary action. In another embodiment, force may be applied to aid filtration. The force can be applied vertically on the filter paper, wherein such forces can include the application of pressure or a vacuum.

The capture membrane can fix the soluble proteins from the individual colonies and their positions on the capture membrane can then be compared to the filter carrying the original colonies. Thus, from the colony filtration blot, it is possible to track back and identify the original colonies expressing the soluble proteins of interest on the growth media. To aid in the process of identifying clones expressing soluble proteins, positive controls can be used. These are clearly seen on the final colony filtration blots and can enable the membrane/blot to be correctly orientated can enable the membrane/blot to be correctly orientated with the original colonies (FIGS. 7 and 8). Hence after the screening step, a solid support such as a capture membrane allows the ready identification of the colonies expressing the soluble proteins of interest.

In another embodiment, the filter with colonies attached can be placed colony side down onto a material soaked in lysis buffer. A (nitrocellulose) capture membrane can then be placed on top of the filter with colonies and several layers of filter paper (and paper towels) can be placed on top of this (FIG. 3a). Force can then be applied to the top of this "sandwich" and ideally transfer buffer poured around the bottom to facilitate filtration and transfer of proteins onto the capture membrane.

In another embodiment the filter is placed colony side up onto a capture membrane and a vacuum is applied to "pull" protein through the filter paper and onto the capture membrane (FIG. 3b).

In practice, lysis and filtration may conveniently take place in one overall step, e.g. during the application of conditions capable of causing lysis (e.g. 3 periods of freeze thawing), the cell lysate is filtered and captured on a capture membrane.

Alternatively viewed, the present invention provides a method of separating soluble from insoluble proteins, which method comprises:

(a) subjecting one or more colonies of cells to conditions which are capable of causing lysis thereof;

(b) filtering the lysate of step (a) through a filter having pores which allow only soluble proteins to pass through the filter, thereby generating a filtrate containing soluble proteins. According to this method, most or all insoluble proteins will fail to pass through the filter and hence separation of soluble from insoluble proteins occurs. It will therefore be appreciated that the filter through which the soluble proteins and the colonies from which they are produced.

Of particular interest is a method of a separating soluble from insoluble membrane originating proteins.

The methods of the present invention can also include the detection of a protein of interest after filtration. Proteins of interest can be detected using various tags which are well known in the art, e.g. histidine tag, VS tag, T7 tag, FLAG tag or any short protein sequence to which a specific antibody is available, glutathione-S-transferase, thioredoxin, green fluorescent protein and maltose-binding protein. Tags are preferably between 1-100 amino acids in length, preferably between 1-70, 2-50, 1-30, or 1-20 amino acids in length. More preferably tags can be 2, 3, 4, 5, 6, 7, 8, 9 or 10 amino acids in length, e.g. His tags are generally 6 amino acids in length.

Tags can be attached to a protein of interest generally by expressing such proteins as fusion proteins. As such, short tags are preferred, to allow proteins of interest to maintain a native-like conformation. Further, C-terminal tags are preferred, although N-terminal His tags are also used. Proteins of interest can also be detected using antibodies, monoclonal or polyclonal, either directed to a tag or directly to the protein of interest (expressed on its own or as a fusion).

Proteins can also be detected if an enzymatic activity is exhibited, for example fusion tags that possess enzymatic activity include green fluorescent protein, horseradish peroxidase and glutathione-S-transferase. Proteins can further be detected via fusion tags which act as the substrate in enzymatic detection methods. Preferably target proteins are not detected on the basis of their own enzymatic activity. If the different colonies are each representative of a particular variant from a generated library, proteins of interest will typically be soluble members of the library. Conveniently therefore the members of the library will be expressed as fusions with a small tag to aid detection or antibodies to the library members may be used.

The filtrates of soluble proteins can further be used in assays to test for the biochemical activity of the protein of interest. In one embodiment, the filtrate can be simultaneously screened for the presence/amount of a soluble protein of interest (e.g. using a tag and an antibody directed thereto) and for the activity of that protein using a suitable assay. If such an assay is performed it will (preferably) be in addition to a method detecting soluble variants, e.g. a method based on affinity binding.

Upon identification of a positive colony (i.e. one expressing a target protein in soluble form), such colonies can be cultured and soluble or total protein isolated for Western blotting if confirmation of the screening results are required. Such clones can be used for the overexpression of the protein of interest for many different purposes, e.g. for structural studies to elucidate the protein sequence.

The methods of the invention are of utility in the separation of soluble and insoluble proteins and for the detection of colonies producing soluble proteins. Soluble proteins can often be expressed in greater amounts and can be used in techniques such as NMR/X-ray crystallography for structural genomics. The methods of the present invention can also be used to screen cDNA libraries for particular clones expressing soluble proteins. The invention can also be used to screen for soluble variants of a particular protein for example, a membrane protein.

The methods of the invention can also be used to screen vector libraries and libraries composed of different expression bacteria or strains. Many standard expression vectors provide poor protein expression due to sequence variation in the promoter regions, translation initiation sites and reporter proteins. By randomising these regions and varying reporter proteins the most efficient sequence for soluble protein expression can be selected.

One example of randomisation of these regions is shown in a recent study where it was demonstrated that translation initiation sites in vectors can vary dramatically depending on the sequence context (Zhelyabovskaya et al. Nucleic acid research. 2004). Studies of different N-terminal fusion proteins have shown a great variation in protein expression levels and solubility. It is thought that the region between the start codon (ATG) and the cloned gene of interest is important for the level of soluble protein expression.

Another way to increase the level of soluble protein expression is to vary expression strains. There are several commercial available expression strains, which can be mixed and the most efficient strain or bacteria selected with the CoFi-blot method. Even in 1943 it was known that spontaneous mutations occurred randomly in an exponentially growing bacterial culture. It was clear that mutants in growing cultures arose independent of the environmental agents, rather than being generated by any agent. When expressing target proteins a variation in expression levels and solubility among bacteria can be seen and it is thought that some of the differences may be a result of differences in genotype of the bacteria. To increase the genomic mutation rate and thereby try to improve expression and solubilisation even more expression strains can be treated with mutagenic agents and high expressing soluble proteins selected using the CoFi-blot technique.

Filtration is performed so that the majority of proteins passing through the filter, in particular the majority of a target protein or proteins passing through the filter are in soluble form. The filter hence acts as the detection screen for this invention, allowing colonies expressing soluble target proteins to be identified.

Genes/cDNAs/coding regions encoding a protein of interest can be mutated to produce variants of that protein with varying degrees of solubility. These mutants can be produced in an expression system, wherein the most soluble variants can be selected using the lysis and filtration steps of the present methods performed on transformed colonies. Genes/cDNAs/coding regions can be transformed or transfected into expression systems in vectors/constructs, such as plasmids, viral vectors, cosmids and YACs. Such vectors may contain regulatory sequences and other elements well known in the art. For example, the gene/cDNA/coding region may be placed under the control of a promoter in a vector. Promoters used are generally capable of expressing the protein of interest within a particular host. In a specific embodiment, the promoter used is inducible i.e. the expression of the protein of interest can be controlled. Such inducible promoters/systems include lac wherein induction of expression is controlled by the addition of IPTG and tet on/off, wherein induction of expression is controlled by the presence/absence of tetracycline and others are known in the field.

Many different methods of mutagenesis are known in the art which could be employed to create a library of variants of a protein of interest. Possible procedures include truncation of the sequence, use of an exonuclease enzyme, introduction of a randomised cassette or site-directed mutagenesis. For truncation, the number of nucleotides removed may be less than 2000, preferably less than 1000, and more preferably less than 800. Introduction of a randomised cassette for mutagenesis preferably uses a cassette containing less than 100 nucleotides.

Mutagenesis is preferably carried out on several copies of a nucleic acid sequence encoding a protein of interest so that a set of different mutated sequences can be screened, hence increasing the probability of identifying a native-like protein with improved solubility. The use of random mutagenesis is especially preferred where there is no prior knowledge of which particular mutations may yield a soluble variant.

Libraries of proteins can be created where the coding region has been randomly mutagenised and where different length constructs have been generated by erase-a-base or random priming reactions.

Further, vectors can be randomly mutagenised (or vector libraries), preferably in the promoter region. N or C terminal tags or in the origin of replication and hosts can be randomly mutagenised, for example by random knockouts or from preselected libraries of strains. The methods of the invention can hence be used to screen directly for the expression of soluble protein from a limited number of genes (transferring cells with just cloned genes) or to screen large numbers of genes e.g. from cDNA expression libraries.

In a further embodiment, the present invention provides a kit for use in the methods described above which comprises:
(a) a filter having pore sizes which only allow soluble proteins to pass through the filter;
(b) a capture membrane; and optionally (c) reagents for use in native lysis of the cell colonies. As discussed above, (b) is preferably a nitrocellulose membrane and (c) preferably includes one or more components of a native lysis buffer as described herein. Suitable filters and capture membranes are also discussed herein. Optionally the kit also contains (d) detection means, e.g. affinity binding partners, for the target protein of interest. Such kits can be used to detect colonies expressing a soluble variant of a membrane protein.

The invention will now be further described in the following non-limiting Examples.

BRIEF DESCRIPTION OF THE SEVERAL VIEWS OF THE DRAWING(S)

Figure 1:
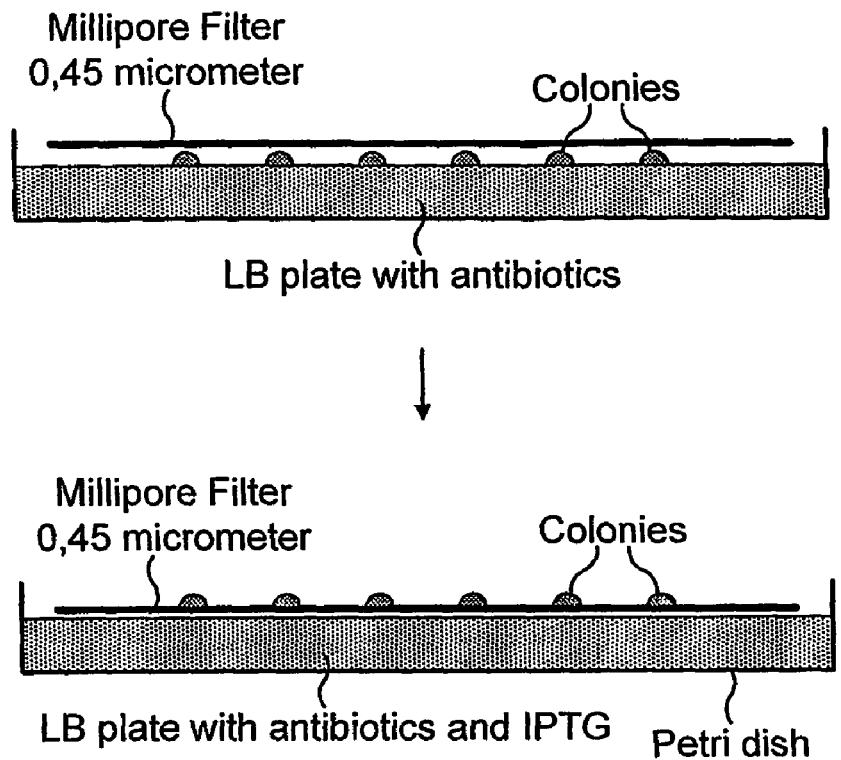
FIG. 1 shows a method of peeling/lifting colonies from the semi-solid/solid growth media using a filter.
Figure 2:
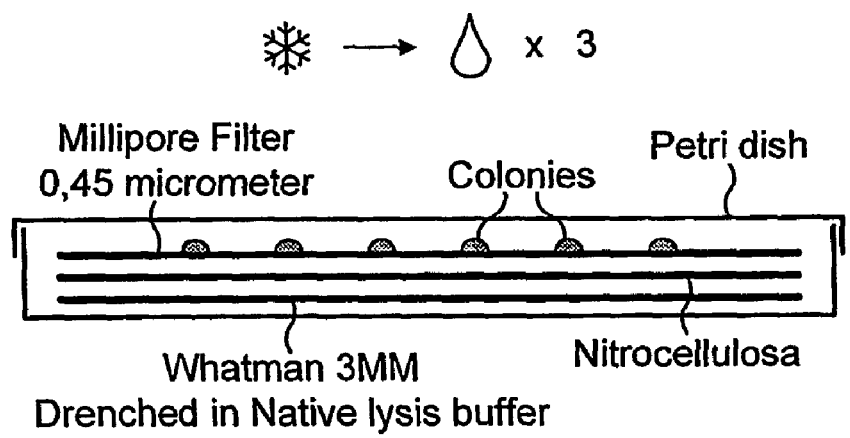
FIG. 2 depicts one procedure to obtain colony lysis, wherein the filter with colonies is placed colony side up onto nitrocellulose and the filter soaked in native lysis buffer; following lysis of the colonies, soluble proteins can pass through the filter onto the membrane.
Figure 3A:
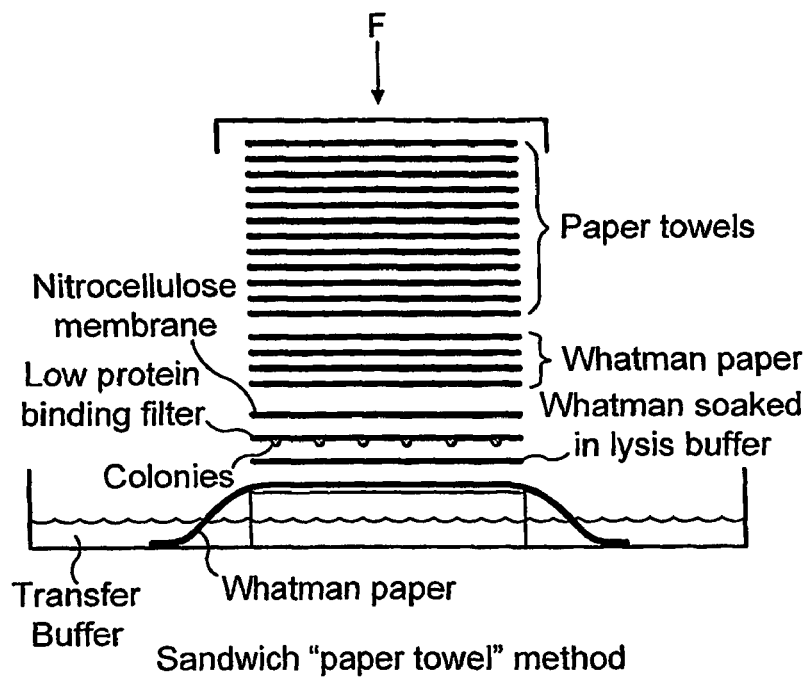
Figure 3B:
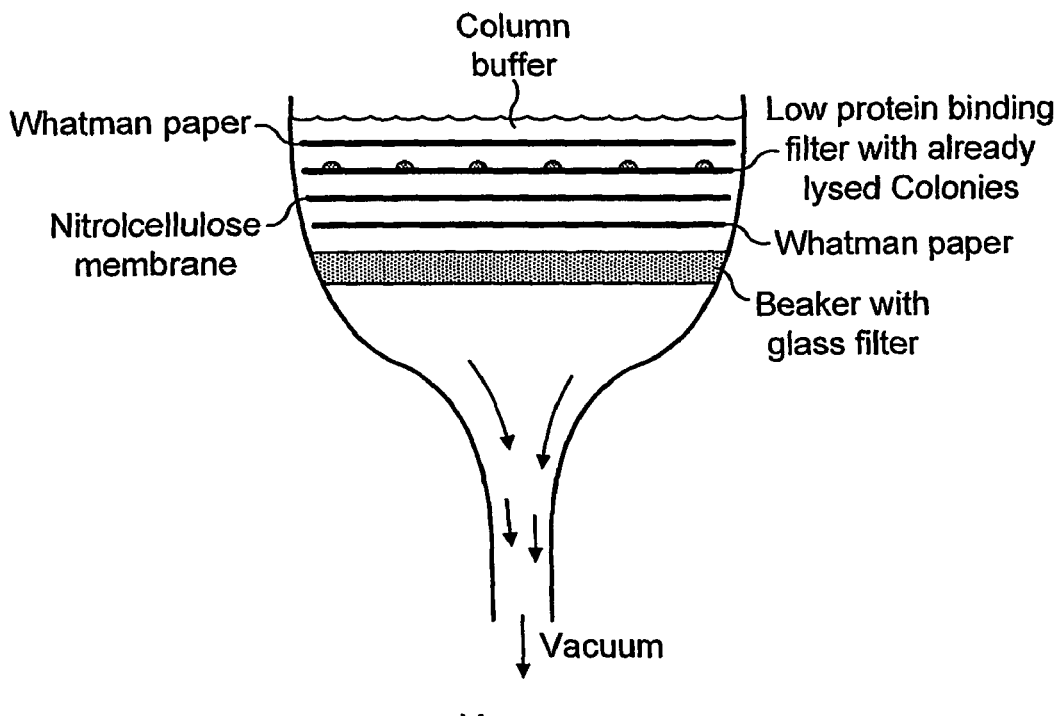
Figure 4A:
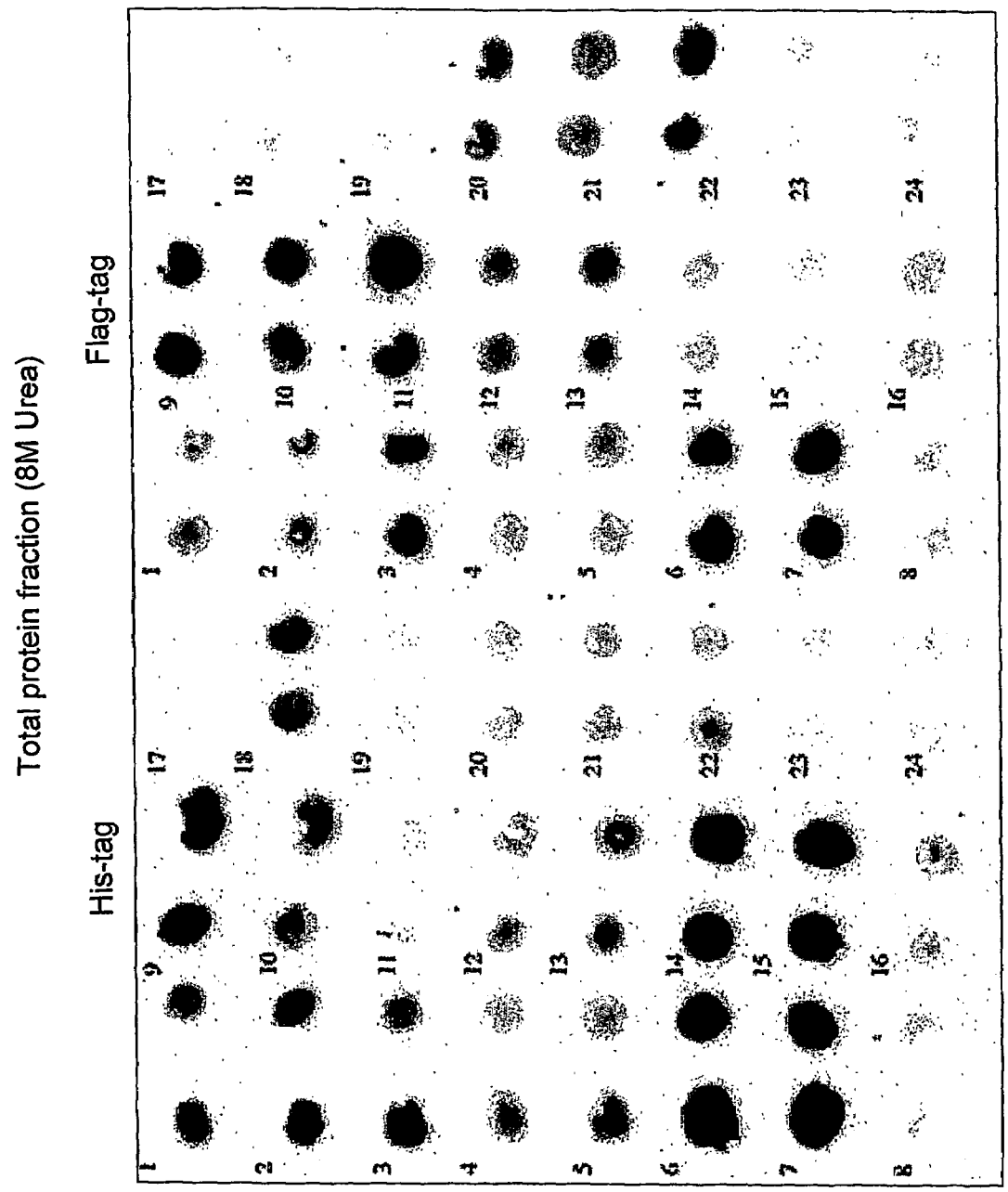
Figure 4B:
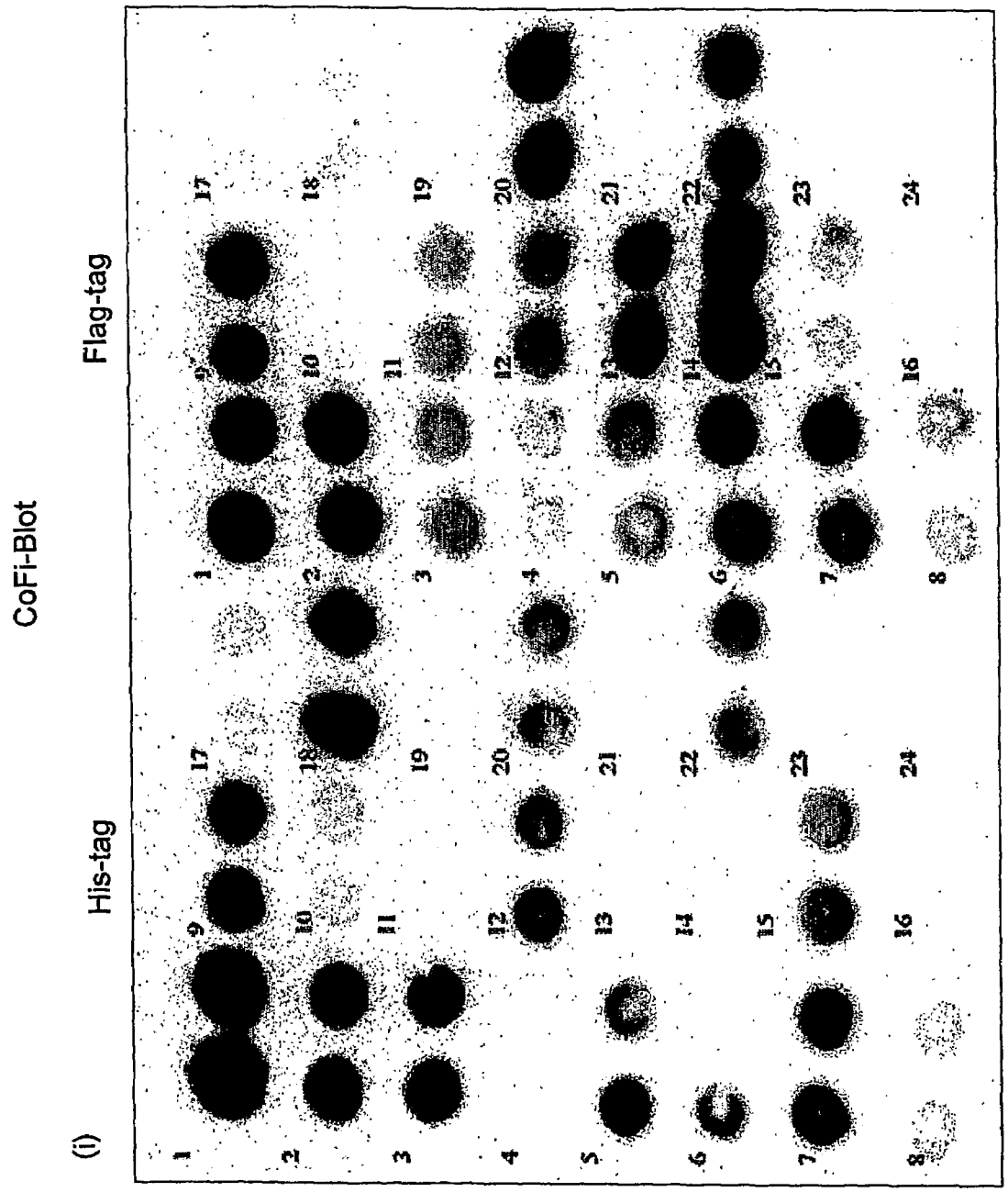
Figure 4C:
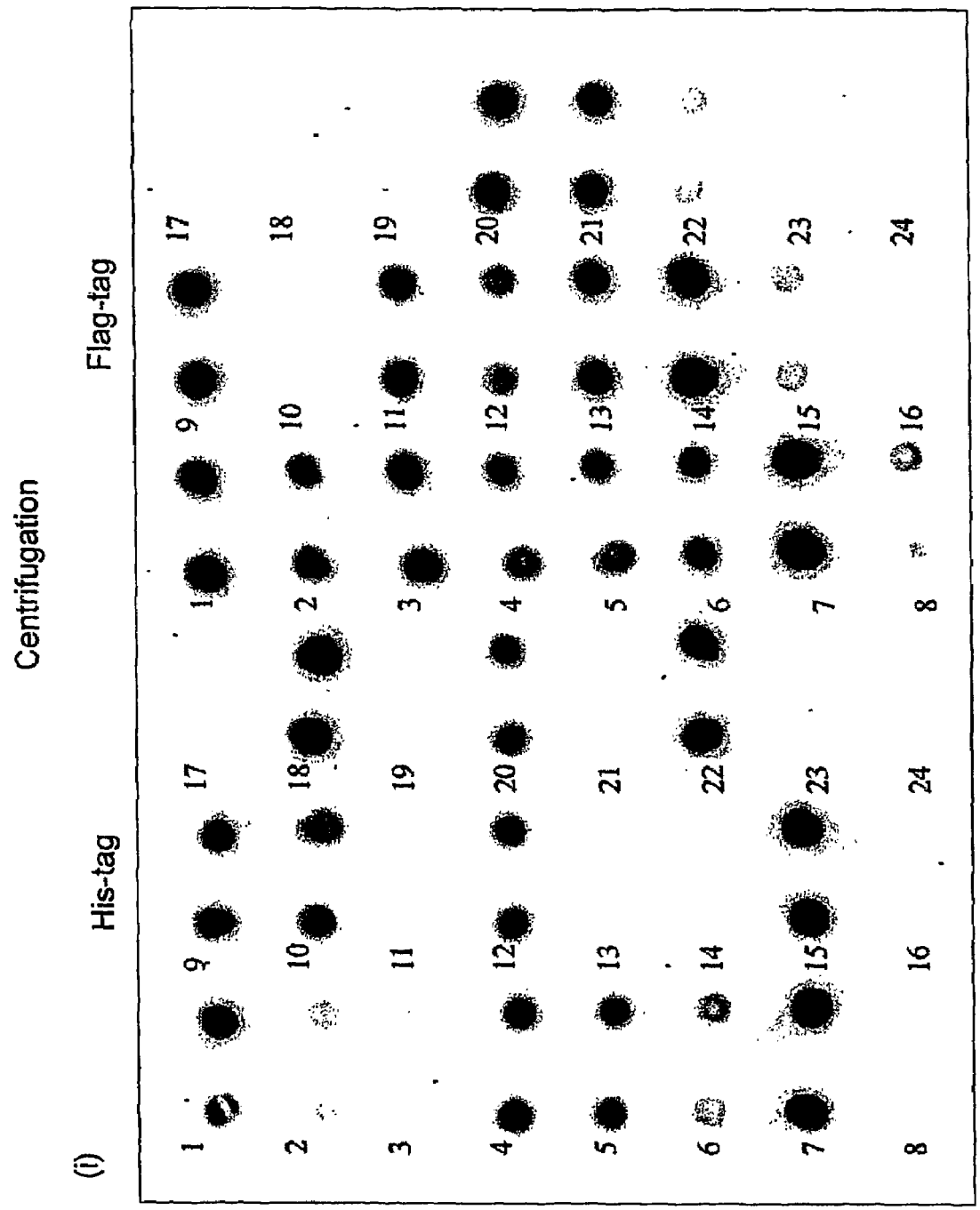

FIG. 3a shows one embodiment of the invention where the "sandwich" method is employed. A filter with colonies is placed colony side down on filters soaked in lysis buffer. Nitrocellulose is placed on top of this and filter paper and paper towels on top of this. A force is then applied;

FIG. 3b shows another embodiment of the invention where a filter with colonies is placed colony side up on a nitrocellulose membrane in a column with buffer. A vacuum is then applied to aid filtration;

FIG. 4a shows a colony filtration blot for total protein for all 48 different constructs used to screen for soluble proteins of 24 E. coli proteins;

FIG. 4b (i) shows a colony filtration blot of the 48 constructs (24 different E. coli proteins with either an N-terminal His or flag tag), where positive colonies (hence soluble) can be seen; (ii) shows a table describing the expression levels of each protein in the colony blot, where these levels were compared to the values of the centrifugation blot (71% were predicted in the right category and only 8% were either false positives or false negatives);

FIG. 4c (i) shows a dot blot for the same 48 constructs, wherein soluble protein fractions have been isolated by centrifugation; (ii) shows a table describing the expression levels of each protein in the centrifugation blot.

Figure 5:
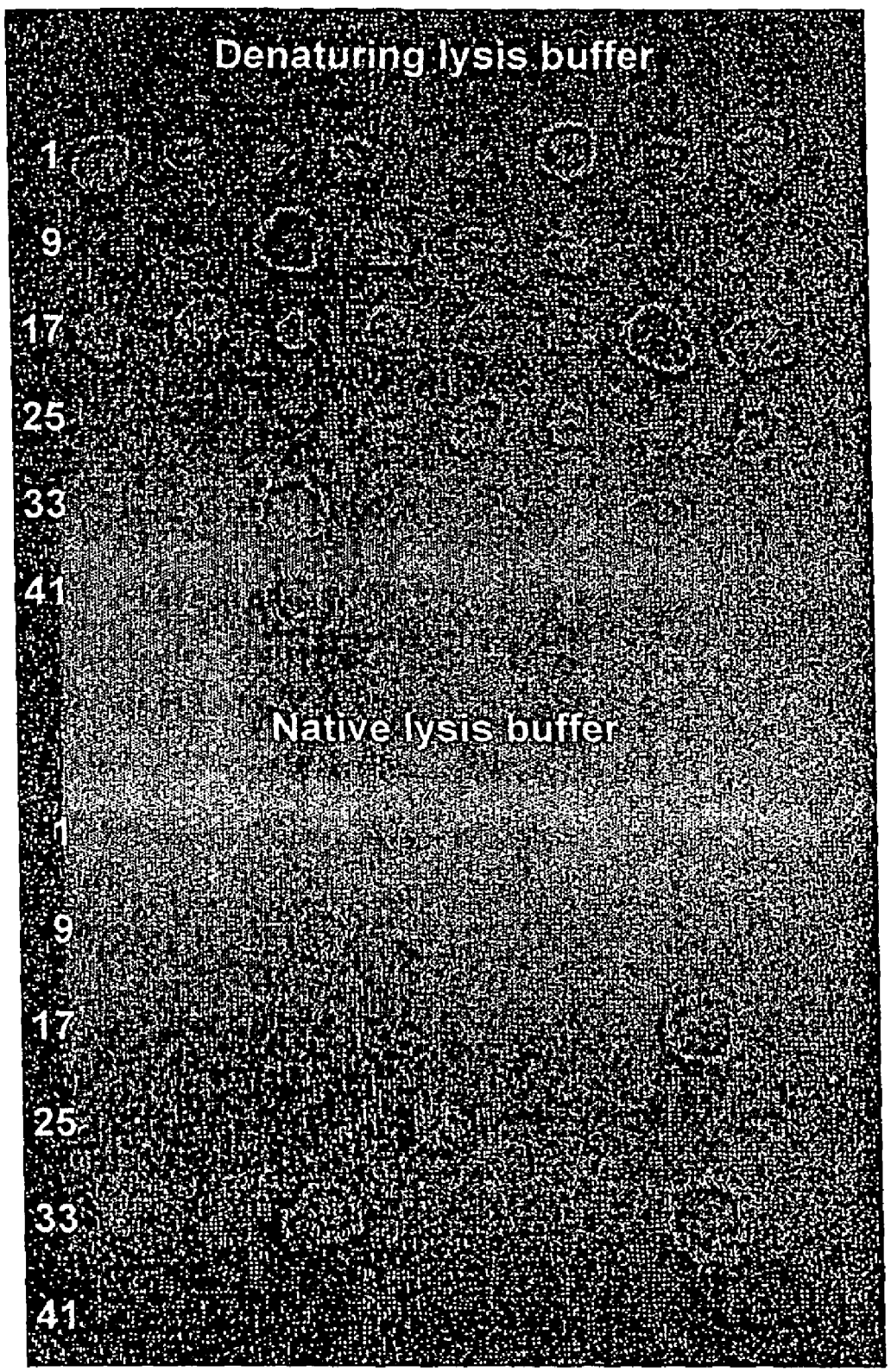
Figure 6:
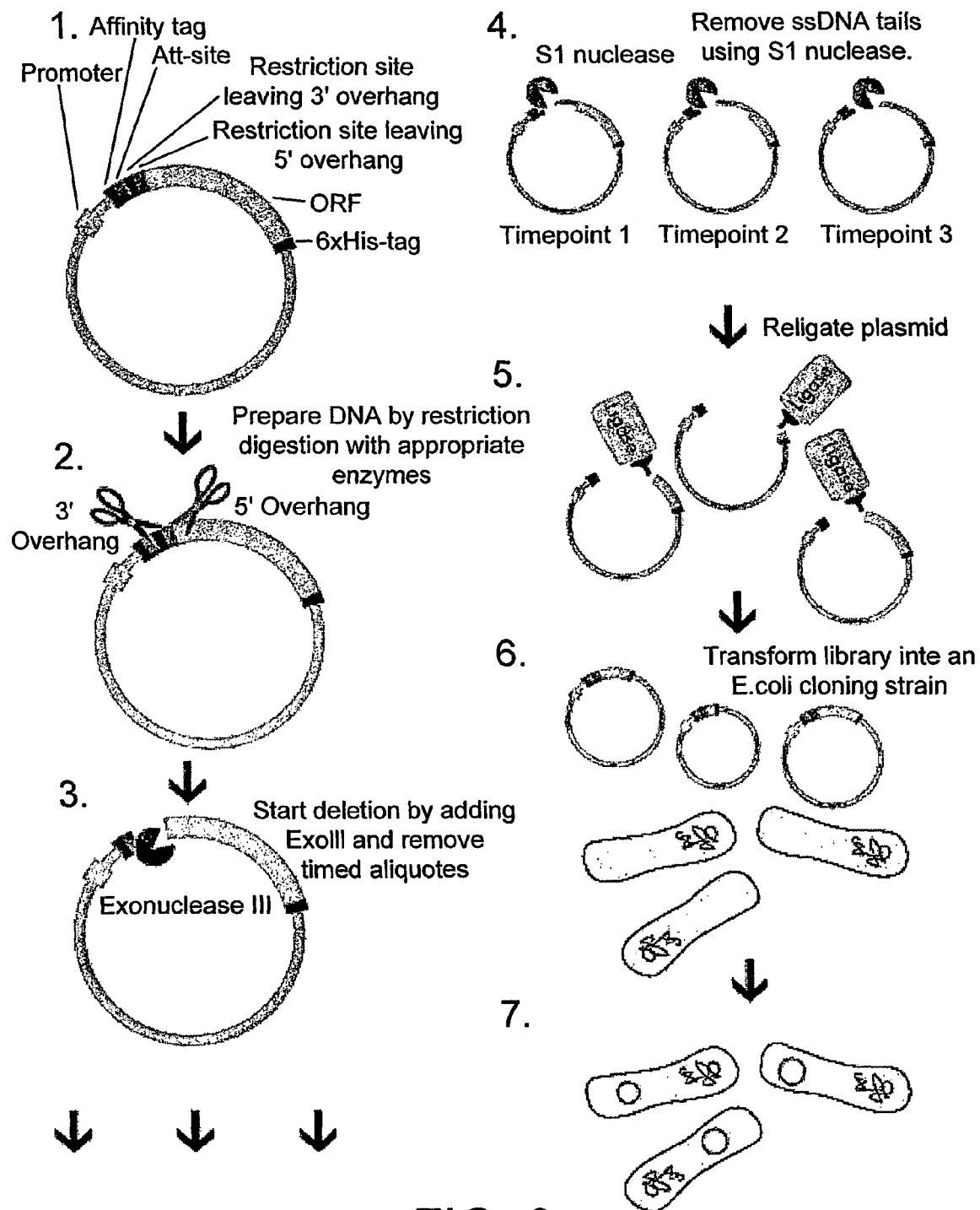
Figure 7A:
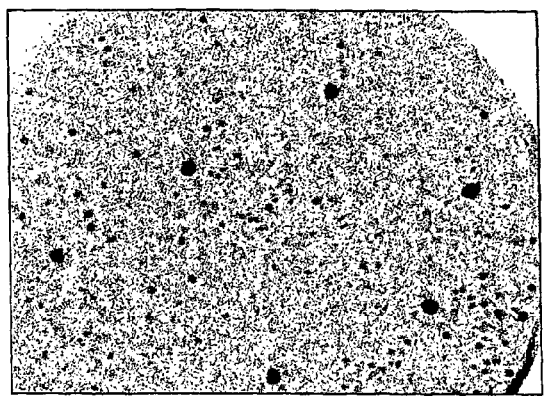
Figure 7A:
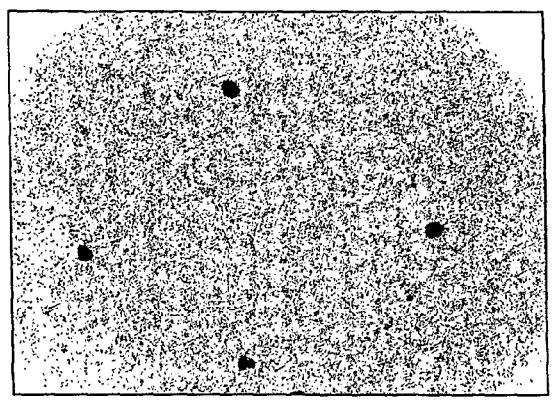
Figure 7A:
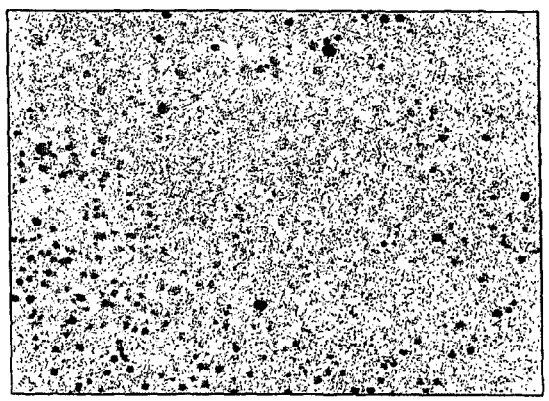
Figure 7A:
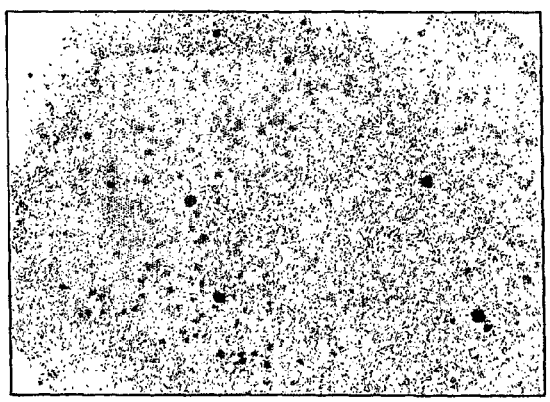
Figure 7B:
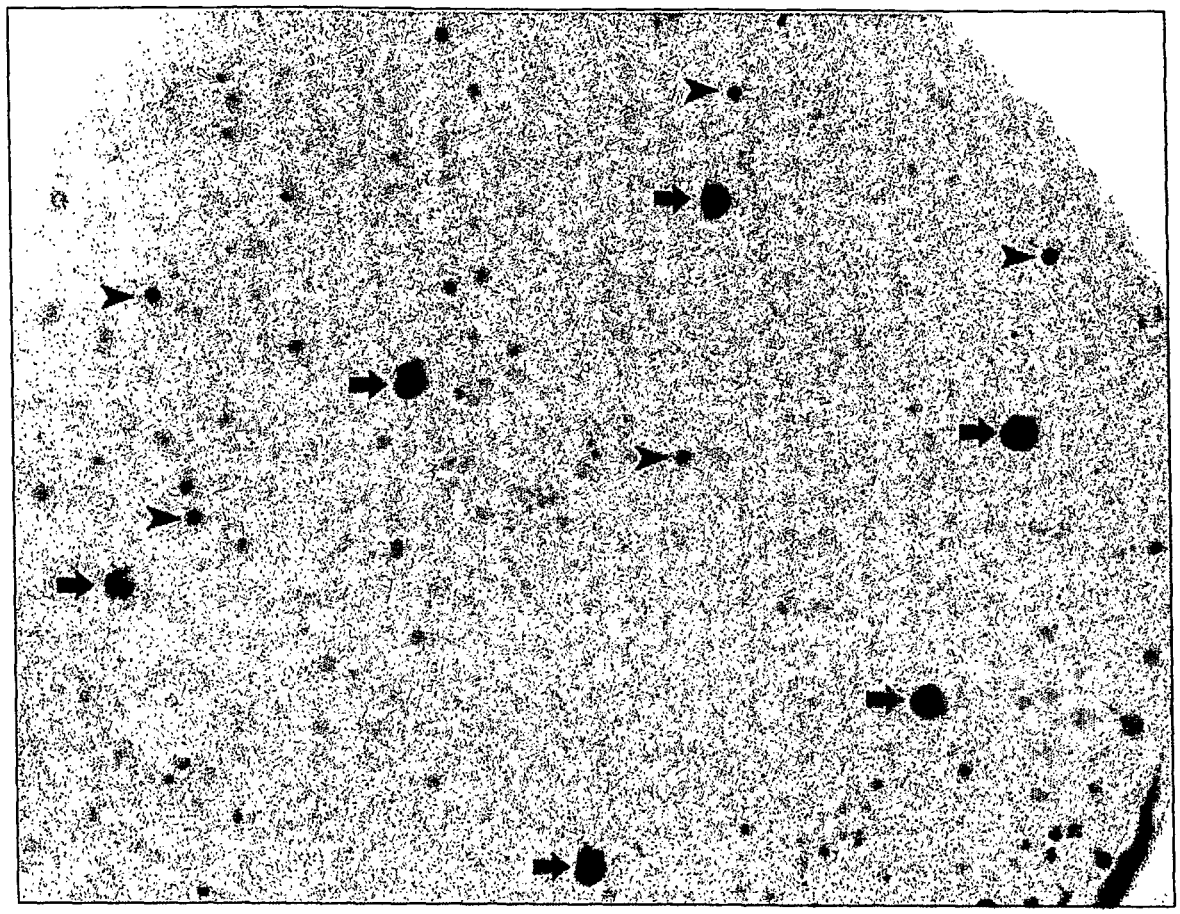
Figure 8:
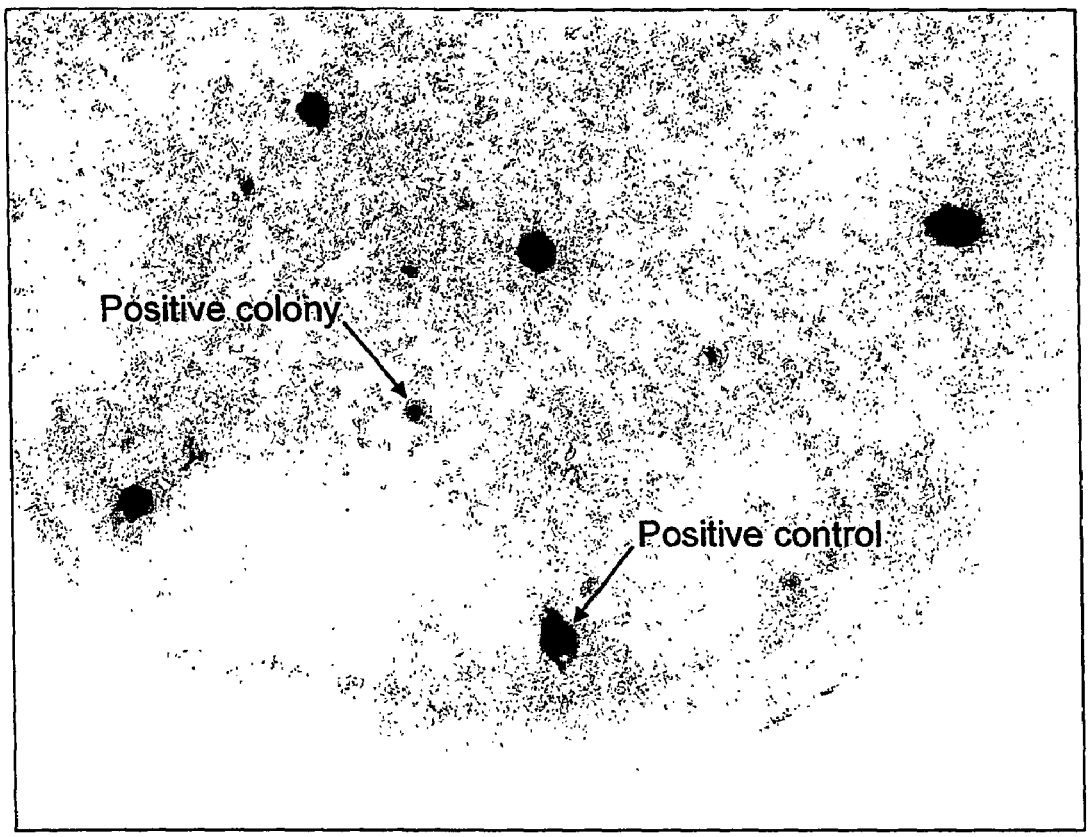
Figure 8:
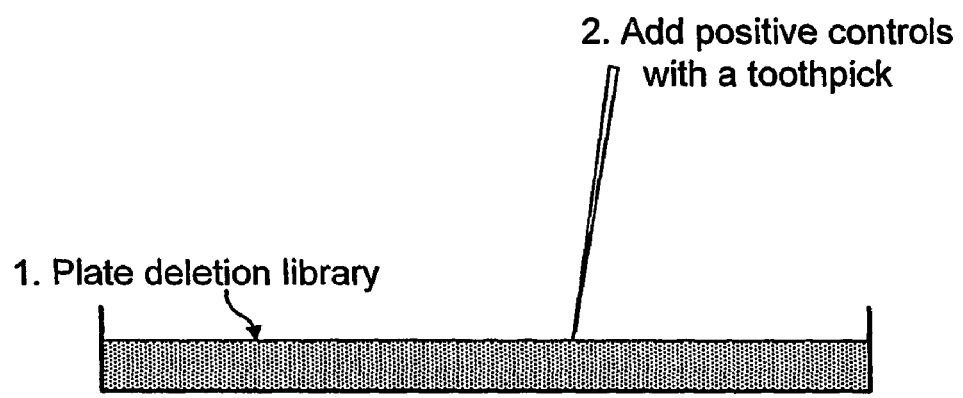
Figure 9:
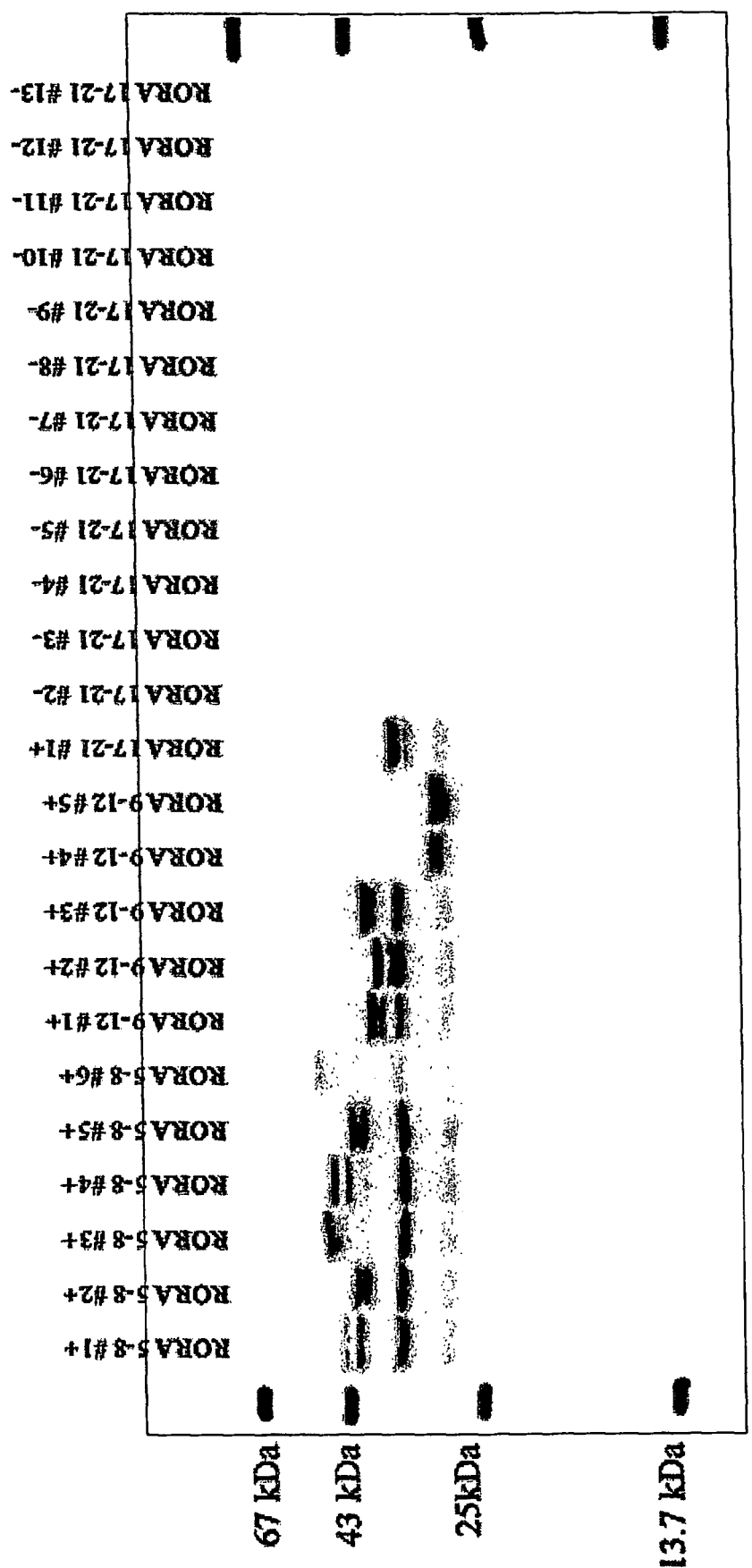
Figure 10:
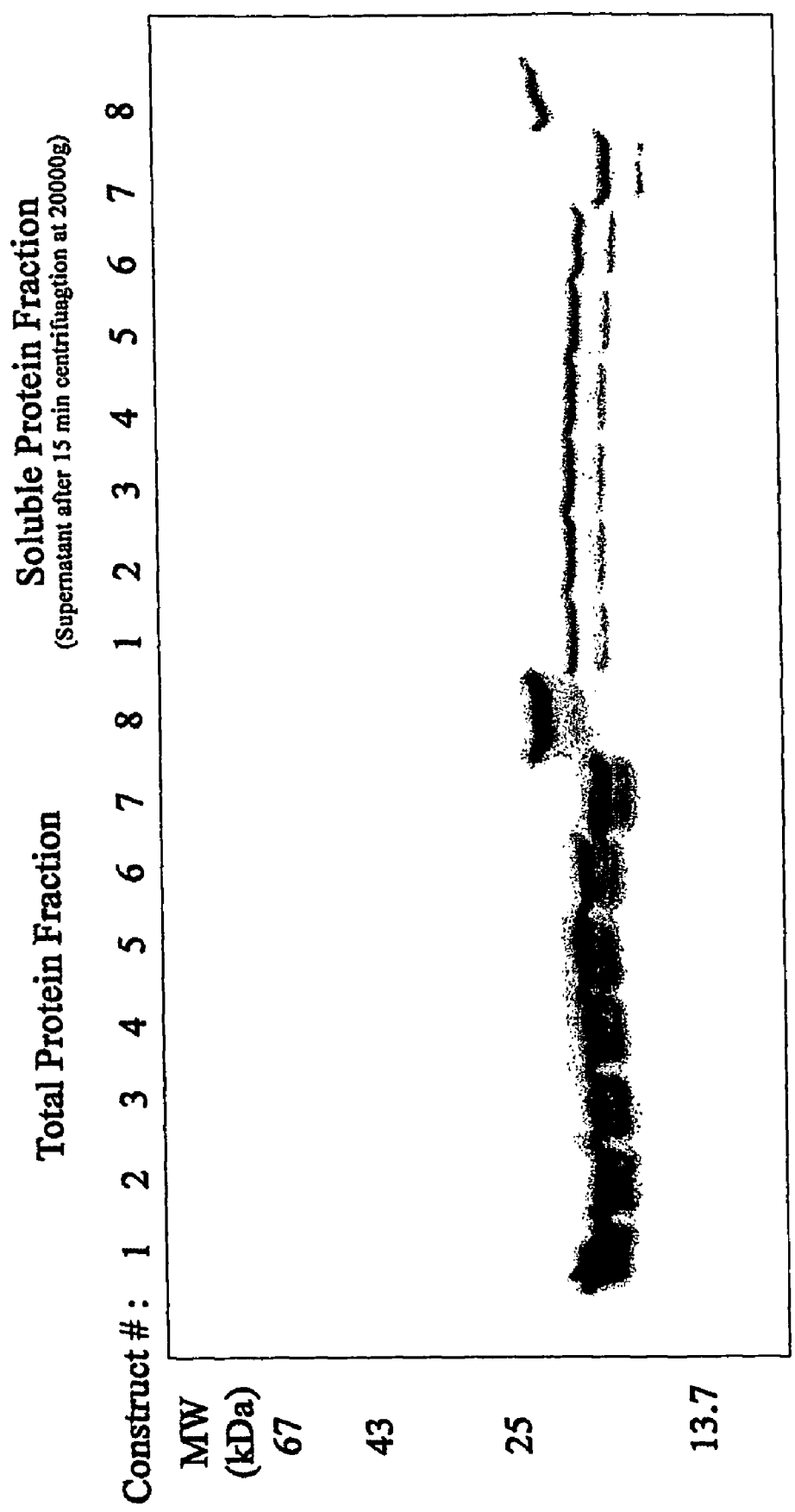
Figure 11:
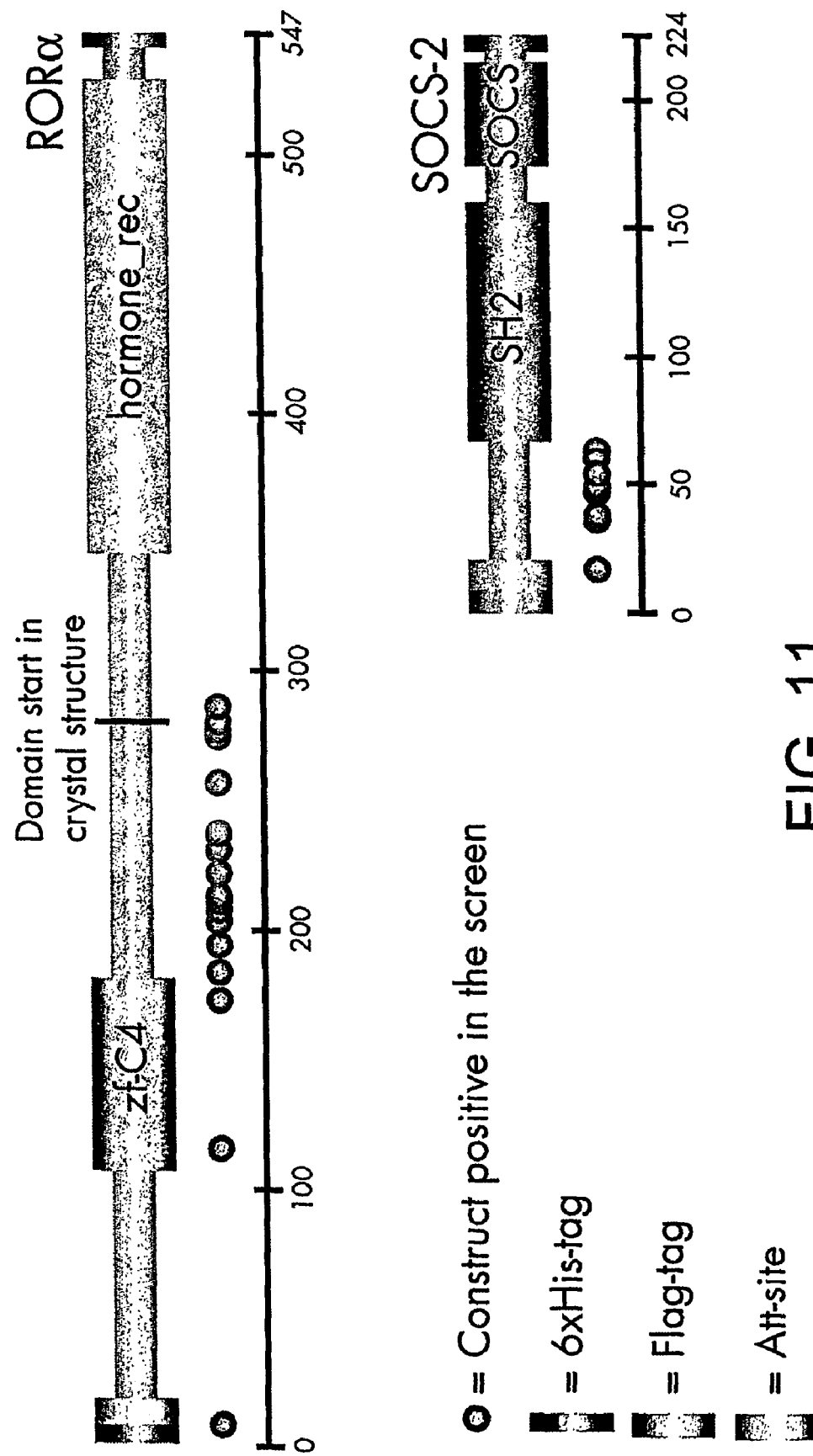

FIG. 5 shows results of a dot blot comparing the number of positive GST tagged clones obtained when denaturing or native lysis buffer is used;

FIG. 6 shows a schematic presentation of the Erase-A-Base process; the plasmid is linearized by endonuclease digestion in two unique restriction sites introduced in the cloning primer (2); the enzymes are chosen in such a way that one leaves a 3' overhang protected from ExoIII digestion and one leaves 5' which is susceptible to the digestion; samples from the ExoIII digestion are removed at timed intervals (3) and added to tubes containing S1 Nuclease, which removes the remaining single-stranded tails (4); the plasmid is religated (5) and transformed into a E. coli cloning strain (6, 7); the library is then recovered from the cloning strain and transformed into an expression strain and screened for soluble expression;

FIG. 7a shows examples of four different colony filtration blots; two blots that are from the RORa library and two from the SOCS-2 library; the time points where the aliquots were removed are noted under the pictures; the later time points do not contain any or very few colonies judged as positives; this is due to the fact that constructs at these time points correspond to proteins which have their start inside a domain;

FIG. 7b shows RORA 5-8 minutes in more detail, where the positive controls are located and some examples of colonies judged as positive/soluble;

FIG. 8 shows positive controls being added to a plated library; positive controls will form positive colonies and can serve as reference points to help identify other positive colonies expressing soluble protein;

FIG. 9 shows Western blot of soluble protein fractions of 24 different clones picked from a filtration colony screen of RORa library; the cells were grown in liquid culture and lysed using freeze thawing; the insoluble material was pelleted using centrifugation at 20000 g for 15 minutes; + indicates that the clone was judged as soluble from the screen; − indicates that the clone was judged as insoluble from the screen;

FIG. 10 shows Western blot of eight clones identified as soluble from the colony filtration screen of a SOCS-2 library; the cells were grown in liquid culture and lysed using freeze thawing and the insoluble material was pelleted using centrifugation at 20000 g for 15 minutes; all eight clones show soluble protein expression;

FIG. 11 shows a schematic presentation of the protein domain organisation of RORa and SOCS-2; the green circles show the start position of clones identified as soluble in the colony filtration screen of the libraries; interestingly the start positions of these clones are all located in between domain borders.

Figure 12:
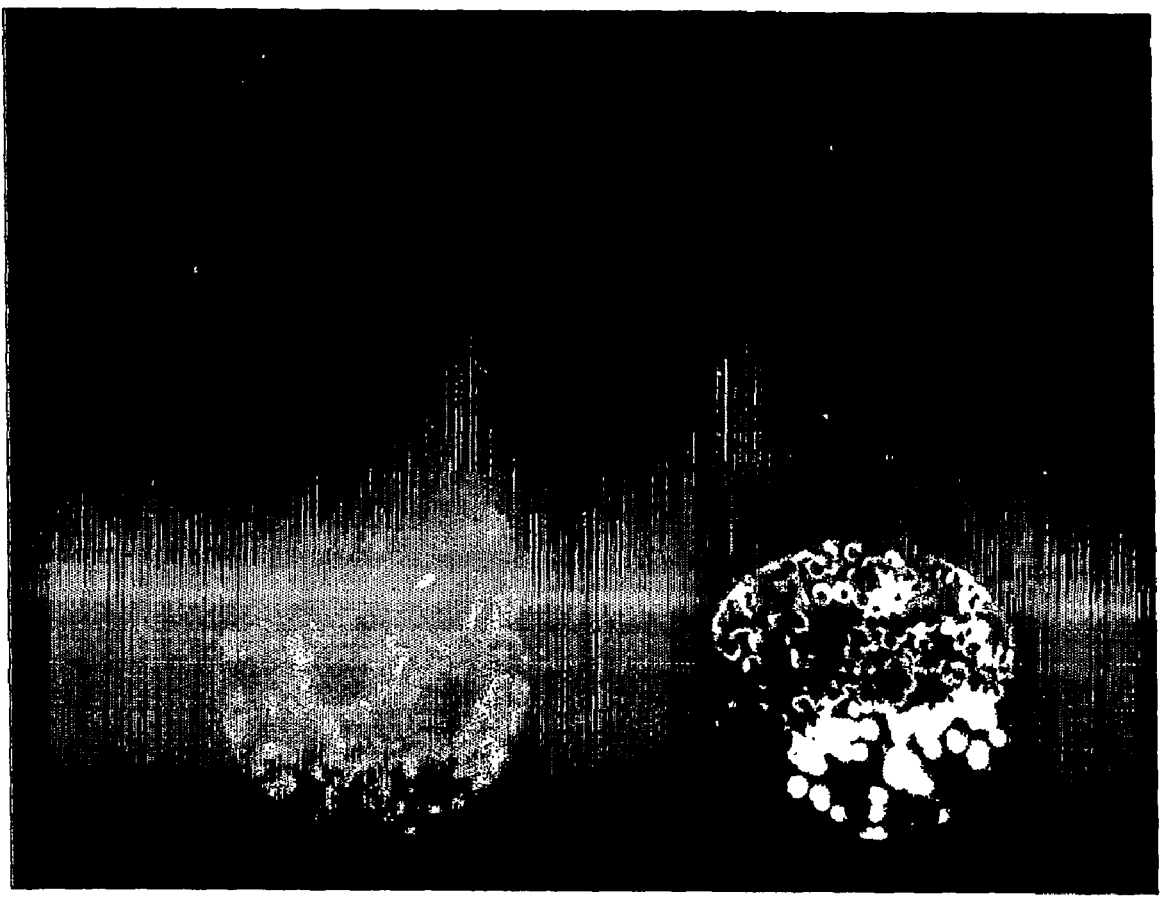

FIG. 12 shows colony filtration blot for an E. coli integral membrane protein predicted to contain 13 transmembrane segments (amino acid permease) in a) native lysis buffer (as in Example 1) b) denaturing lysis buffer (+8M Urea) c) +Triton X-100 (1%) d) dodecylmaltoside (5 mM).

Figure 13A:
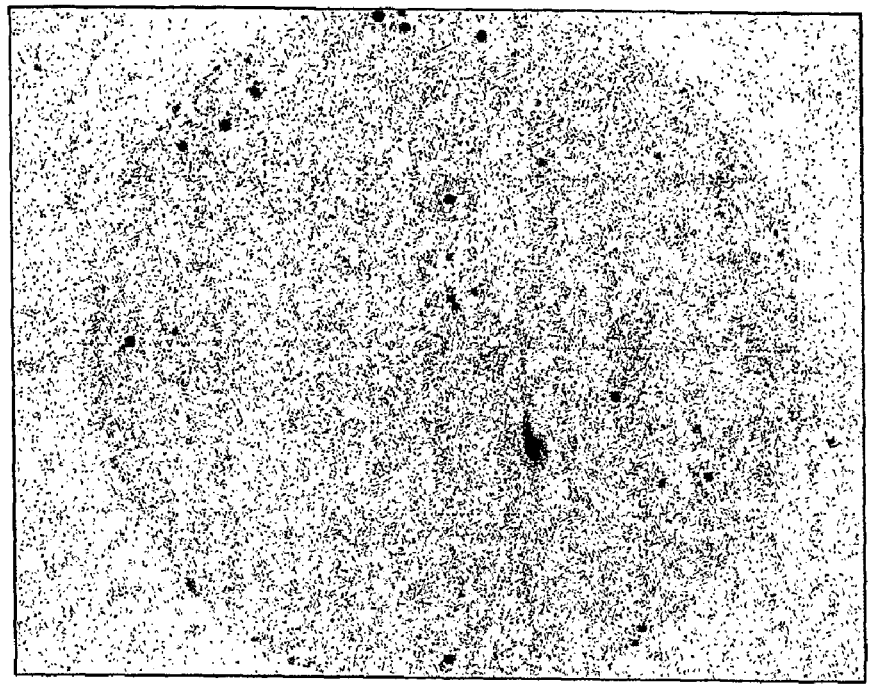
Figure 13B:
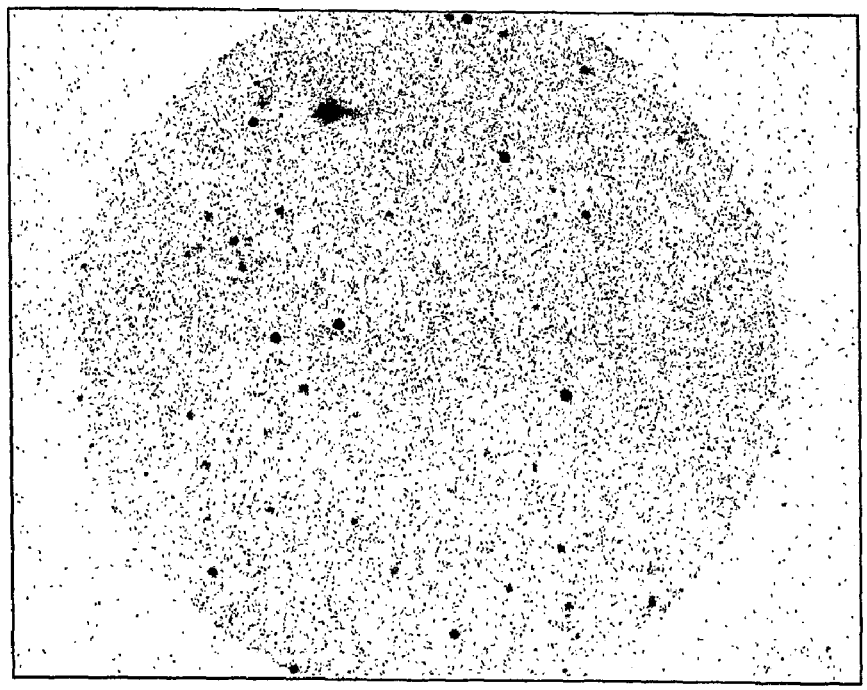

FIGS. 13a and 13b show colony filtration blots of mutation libraries of two different E. coli membrane proteins (a and b). Positive and surrounding colonies were picked for further analysis.

Figure 14A:
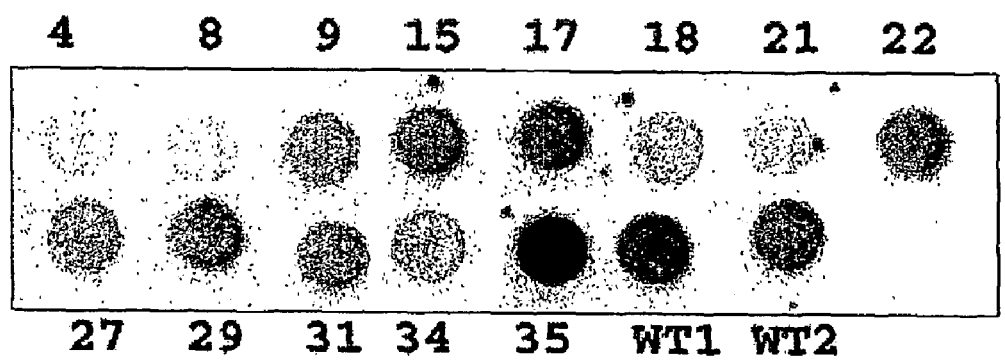
Figure 14B:
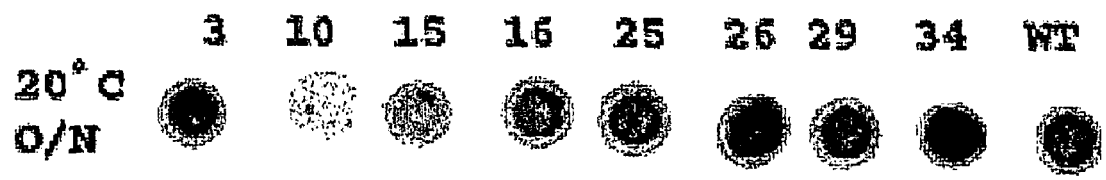

FIGS. 14a and 14b show dot blots made of the soluble fractions from clones picked from the colony filtration blots of FIGS. 13a and 13b. The non-mutated wild type (WT) protein was included on the blots. An increase in membrane protein expression as compared to the WT can be seen among several of the clones from both proteins (a and b).

EXAMPLES

Example 1

Screening for Soluble Variants

24 E. coli proteins in two different expressions vectors, N-terminal His- or Flag-tag, with known solubility characteristics were used to test the Colony Filtration blot procedure (CoFi blot). The method uses an antibody-reaction for detection of soluble protein, and is therefore universally applicable to any protein containing a suitable tag, or other fusion polypeptide moiety, against which antibodies can be generated.

Materials and Methods

Materials: Chemicals were from ICN (Costa Mesa, Calif., USA) or Sigma-Aldrich Sweden (Stockholm, Sweden), if not stated otherwise. Oligonucleotides for PCR were purchased from Invitrogen.

Cloning of recombinant E. coli clones: DNA-fragments coding for 24 different E. coli proteins were amplified from genomic E. coli DNA by PCR, using specific primers. PCR products were cloned using the Gateway system (Invitrogen) into two pET based expression vectors containing either a N-terminal His-tag or a N-terminal Flag-tag. All constructs contain a C-terminal his-tag used for detection.

Small-scale expression of test clones: For control expression tests, the plasmids were freshly transformed into E. coli strain B121 (DE3), single colonies were picked and grown overnight in LB medium (Difco, Detroit, Mich., USA) at 37° C. while shaking at 250 rpm. For test expression, 1 ml LB was inoculated 1:10 with overnight culture and grown to an $OD_{600}$ of about 0.6. Cultures were induced by addition of IPTG to a final concentration of 1 mM and grown for another 4 h in a shaker running at 250 rpm at 37° C. The cells were harvested by centrifugation at 2000 g.

Culturing on LB media plates: Freshly transformed cells from the 48 different constructs (24 different proteins in two expression vectors) were arrayed on two LB plates containing appropriate antibiotics at 37 degrees. The colonies were transferred to a Durapore filter membrane with 0.45 µm pore size (Millipore, Bedford, Mass., USA) by gently applying the filter membrane on top of the LB plate, thereby putting the filter membrane in contact with the colonies. Through this procedure most of the colonies are transferred to the surface of the filter membrane. The filter membranes were then transferred with the colony side up to a new LB plates containing IPTG resulting in induced expression. After 4 hours the filter membrane containing the colonies was subjected to lysis. The procedure described was done for two membranes in parallel, one to be used for detection of soluble proteins and one to be used to detect total protein, i.e. the sum of the aggregated protein and the soluble protein.

Lysis of colonies and transfer to detection membrane: The lysis for total protein was done by placing one of the filter membranes on top of a "lysis and detection sandwich" constituting of one Protran BA 45 nitrocellulose membrane (Schleicher & Schuell, Dassel, Germany) and a 3MM paper (Whatman) drenched in denaturing lysis buffer. (8M Urea, 20 mM Tris, pH 8, 100 mM NaCl). The colonies are subjected to this treatment for 1 hour at room temperature.

For lysis under non-denaturing conditions the second membrane was placed on a similar sandwich soaked in native lysis buffer containing 20 mM Tris, pH 8, 100 mM NaCl, lysozyme (200 µg/ml=2.35 Units/ml) and DNAse I (750 µg/ml=487.5 Units/ml). The "lysis and detection sandwich" is then frozen at −80° C. for 10 minutes and thawed for 10 minutes at 37 degrees. This freeze/thaw procedure is repeated 3 times.

Solubility assay, dot-blots: For solubility assays, cell pellets from small-scale expression cultures were resuspended in lysis buffer consisting of 20 mM Tris, pH 8, 100 mM NaCl, lysozyme (100 µg/ml=2.35 Units/ml), DNAse I (750 µg/ml=487.5 Units/ml) and freeze/thawed 4 times. The lysates were then centrifuged at 20 000 g for 15 minutes for separation of the soluble protein in the supernatant from insoluble protein (inclusion bodies) precipitating in the pellet.

Samples from the soluble fractions were dotted onto a nitrocellulose membrane (Schleicher & Schuell, Dassel, Germany).

Antibody-incubation and development of colony filtration blots and dot blots: Colony filtration blots and dot blots were treated similarly after transfer of protein to nitrocellulose. Membranes were blocked in 1% BSA in TBST (20 mM Tris, pH 7.5, 500 mM NaCl, 0.05% Tween-20) for 1 h or overnight. The blots were then washed three times for 10 min in TBST. The membranes were incubated for 1 hour with INDIA His Probe (Pierce) diluted 5 000 in TBST. Blots were then washed three times for 10 min in TBST. The membranes were developed using a chemiluminescence solution SuperSignal WEST DURA (Pierce) and the images were captured with a CCD camera (Biorad). The level of expression was quantified using the TotalLab software (Pharmacia biotech)

Results

Confirmation of Soluble Protein Expression by Colony Filtration Blot

Total protein expression was confirmed for the 48 different constructs (FIG. 4a). When the colony filtration blot (FIG. 4b) was compared to the dot blot of the soluble protein fractions after centrifugation analysis (FIG. 4c) only 4 out of 48 constructs were false positives or false negatives. The values of the integrated intensity of the dots were obtained from the TotalLab software. Using the intensities, the dots were categorised into 4 different categorise; No, Low, Medium or High level of soluble protein expression 72% were predicted in the right category. 20% was predicted in the neighbouring category and only 6% in most distant. (Table A)

Example 2

Construction and Screening of Deletion Libraries

To obtain deletion clones, a procedure was employed which has been described before in standard molecular Biology Protocol manuals such as Ausubel et al (Short Protocols in Molecular Biology, 2nd Ed, 1992, ISBN 0-471-57735-9). Here, a commercially available kit from Promega, Madison, Wis., USA (the Erase-a-base® system) was used to perform this reaction step.

To create the library the vector containing the target gene is cut open with restriction enzymes just in front of the gene. The restriction enzymes for this are chosen so they produce suitable 5'- and 3'-ends. The 3'-end is protected from Exonuclease III attack whereas the 5'-end is susceptible to it. Exonuclease III is added and small aliquots at certain time points are removed from the reaction. These aliquots contain constructs of varying length that are religated and transformed into E. coli.

Two different proteins have been subjected to our deletion method coupled to the colony filtration blot.

RORa was until recently an orphan nuclear receptor with no known ligand. In late 2002 the structure of RORa was solved and the ligand was shown to be cholesterol (Kallen J A et. al.). SOCS-2 is involved in negative regulation of cytokine signalling and to date at least three different modulating mechanisms have been demonstrated, one which involves the SOCS-box targeting bound proteins to proteasomal degradation.

Material and Methods

The cDNA clones were chosen from the Mammalian Gene Collection database and ordered from RZDP Deutsches Ressourscenzentrum für Genomforschung.

Cloning

The targets were amplified using Touch down PCR with a plasmid containing the cDNA as template. The PCR primers were designed in such a way that suitable restriction sites were located in front of the open reading frame. The PCR products were cloned into a pET based expression vector using conventional restriction/ligation methods.

Creation of Deletion Libraries

The pET based vectors containing the coding sequence for the two proteins were linearized by endonuclease digestion in the two unique restriction sites introduced in the cloning primer. RORa was digested with SphI and HindIII and SOCS-2 with SphI and XhoI both digestions were made in NEB buffer 2 and at 37 degrees for 3 hours.

The digests were verified by agarose gel electrophoresis and purified (QIAquick PCR Purification Kit, QIAGEN). The Erase-a-Base Kit from Promega was used according to the manufacturers instructions with the following alterations. The Exonuclease III digestions were made at 27 degrees to achieve a rate at of approximately 70 bp/min. 24 aliquots were removed from the ExoIII digestion mix, every minute for RORa and for SOCS-2 every 30 seconds. The 24 samples were pooled into six and treated with S1 nuclease. The DNA was precipitated using Ethanol and Ammoniumacetate. The precipitated DNA was resuspended in 10 mM Tris pH 8 and treated with Klenow polymerase to flush the ends. The plasmids were religated and transformed into a cloning strain, DH5a or Top10 plated on LB plates containing the appropriate antibiotics. The library was recovered from the cloning strain by making a plasmid preparation from the colonies on the plate.

Screening for Soluble Protein Expression

The deletion libraries were transformed into an expression strain BL21 (DE3) and plated onto plates containing the appropriate antibiotics. Positive controls, constructs expressing soluble proteins, were also added to the plate to facilitate orientation. The plates were incubated at 37 degrees overnight. The screening for soluble protein was performed as described in Example 1 with the following exceptions. Expression was induced for 6 hours at 25 degrees instead of 37 and 4 hours. For RORa 12 positive clones and 12 negative clones and for SOCS-2 14 positive clones were taken for further analysis.

Solubility Assay, SDS PAGE and Western Blot Transfer

The clones that were picked for further analysis were characterized as described in Example 1. With the exception that the cells were grown for 6 hours at 25 degrees after induction of expression.

Antibody-Incubation and Development of Colony Blots and Western Blots

The colony blots and western blots were developed as described in Example 1.

Results

Libraries completely covering RORa and SOCS-2 were made and screened for soluble protein expression using our soluble colony blot method. All positive clones (soluble) were confirmed as soluble by conventional methods, e.g. centrifugation, gel electrophoresis and western blots (FIGS. 9 and 10). The clones judged as negative in screen did not give any bands in the Western blot (FIG. 9). Interestingly when the sizes were compared to the PFAM domain structure all soluble clones were located in between predicted domain borders. The last soluble construct in the RORa library appear very close to start of the cholesterol-binding domain seen in the crystal structure (FIG. 11).

Example 3

Constructions and Screening of a Library of Membrane Proteins

Cloning of recombinant *E. coli* clones: DNA fragments coding for 42 different *E. coli* membrane proteins were amplified from genomic *E. coli* DNA by PCR, using specific primers. PCR products were cloned into Gateway vectors by homologous recombination. The plasmids were transformed into *E. coli* strain C41. Single colonies were picked and grown overnight in LB medium (Difco, Detroit, Mich., USA) at +37° C. while shaking at 200 rpm. Cell stocks were prepared by adding glycerol to cell culture aliquots to the final concentration of 25%, and stored at −80° C.

Culturing on LB media plates: Cells from frozen stocks were resuspended in LB, plated on LB media plates containing an appropriate antibiotic, and grown overnight at 37° C. The colonies were transferred to filter membranes of different type and origin (Millipore, Bedford, Mass., USA; or Pall Life Sciences, Ann Arbor, Mich., USA), or of different pore size (0.45 to 3 μm) by gently placing the filter membrane on top of the LB plate, thereby putting the membrane in contact with the colonies.

The filter membrane were then transferred with the colony side up to a new LB plate containing IPTG for induced expression at +37° C. for 3 hours.

Lysis of colonies and transfer to detection membrane: Lysis under native and denaturing conditions was performed as described in example 1, for 60-90 min. Lysis in presence of detergents was performed in the same way as the native lysis in Example 1, except Triton X-100 (1%) or dodecylmaltoside (5 mM) was added to the native lysis buffer. Detection was done using an antibody specific for a C-terminal His-tag.

Results

The membrane proteins from the colonies which were lysed in a native lysis buffer with detergent present were clearly visible in the blots, while proteins from colonies lysed without detergent present were not visible (See FIG. 12). The addition of detergent solubilised membrane proteins allowing them to pass the filtration membrane and to be visible on the colony blot.

Example 4

Random Mutagenesis of Membrane Proteins Coupled with Expression Screening Using the Colony Filtration Blot Mutagenesis:

PCR reactions were performed with a Gene-amp PCR system 9700 thermocycler. Mutagenesis was performed with Stratagen GeneMorph Random Mutagenesis kit (Stratagen, La Jolla, USA) according to manufacturer's protocol for medium range mutation frequency (3-7 mutations/kb). The PCR program suggested in manufacturer's manual was used with a denaturing temperature of 94° C. and an annealing temperature of 55° C.

Cloning and Creation of Libraries:

The PCR products were cloned into an expression plasmid, transformed into DH5α ultracompetent cells and plated on LA plates with tetracyclin (30 µg/ml). After overnight growth, the colonies were pooled using 9 ml of LB, and plasmid DNA was isolated using a miniprep kit according to manufacturer's protocol. Plasmids were transformed into a C41 expression system and plated on LA plates with tetracyclin (30 µg/ml).

Expression Screening:

Expression screening of the libraries was performed as described in Example 3 with the following exception: The detergent n-dodecyl-β-Maltopyranoside (DDM) was used instead of Triton X-100 and the membrane was probed using India HisProbe-HRP (Pierce) as described in Example 1.

Small-Scale Expression and Estimation of Expression Levels by Dot Blots

Clones of interest were grown in liquid culture as described in example 1 and the cells were lysed as described in example 1 with the exception that DDM was added to the lysis buffer. Dot blots were made of the solubilized fractions. The dot blots were developed as described above.

Results

Random mutagenesis was performed on two E. coli membrane proteins with very low level of protein expression. The libraries containing the mutated proteins were screened using the colony filtration blot (FIG. 13). Clones that showed an increase in the level of membrane proteins capable of being made soluble were identified. The increase in the level of expression, compared to wild type (WT), was confirmed by dot-blots of the solubilized membrane protein (FIG. 14).

Example 5

To evaluate randomisation of the region between the start codon and the gene of interest, a vector library can be designed consisting of a randomised stretch of five amino acids adjacent to the start codon. This creates a great vector variation and ideally the randomised region can be fitted individually to the different protein targets. The randomised nucleotides after the ATG in the expression vector can either be added to the vector directly or added together with the gene of interest by cloning of a PCR product generated from randomised primers. The principle of primer design for adding randomised nucleotides is ATG NNN NNN NNN NNN NNN [SEQ ID NO: 1]. The selection of highly expressing soluble clones will be performed as described with the CoFi-blot technique.

Example 6

Random Genomic Mutagenesis of Expression Strains

The genomic mutagenesis was performed with 2AP (2-aminopurine) on Rosetta 2 (DE3) as described in the work of Miller (Miller et al. 1992. A short course in bacterial genetics. A Laboratory Manual and Handbook for *Escherichi coli* and related bacteria, Cold Spring harbour laboratory press, Cold Spring Harbour, N.Y., 1992). 2-Aminopurine (2AP) was used at a concentration of 700 g/ml-1000 µg/ml. Cultures were prepared by subculturing $10^4$, to $10^5$ into 3 ml of LB with and without 2AP (without 2AP for viability test), both cultures were grown for 12 to 16 generations in LB before plating. Mutagenesis was done both on empty bacteria and on bacteria containing expression vectors with target genes. The mutator frequencies were determined by the Rifr (Rifampicin revertants) method described by Miller (Miller et al. 1992 supra) where the mutation frequencies should optimally be in the range of $10_{-4}$-$10_{-3}$. Rifampicins inhibit the RNA polymerase and thereby cell growth. The mutation frequencies were calculated as the amount of revertants growing on Rif containing plates compared to the number of viable cells. Mutant expression strain libraries were screened with the CoFi-blot technique as described above.

The invention claimed is:

1. A method of identifying a cell colony which expresses a soluble variant of a target protein, which method comprises:
   (a) subjecting said cell colony to conditions which are capable of causing non-denaturing lysis thereof, wherein said lysis is carried out chemically, by freeze-thawing colonies or a combination thereof, and wherein said cell colony is not grown in liquid culture;
   (b) filtering the lysate of step (a) through a filter having pores which allow only soluble proteins to pass through the filter; and
   (c) detecting target protein which has passed through the filter, wherein the target protein is not detected on the basis of its own enzymatic activity.

2. The method of claim 1 wherein lysis is carried out by freeze thawing colonies.

3. The method of claim 1 or 2 wherein lysis is carried out using a lysis buffer.

4. The method of claim 1, wherein the target protein is fused to a protein or polypeptide tag.

5. The method of claim 1, wherein soluble proteins in the filtrate are identified using antibodies and/or fusion tags.

6. The method of claim 4 or 5 wherein the fusion tag is His.

7. The method of claim 4, wherein the tag acts as the substrate in an enzymatic detection method for detecting the target protein in step (c) of claim 1.

8. The method of claim 1, wherein step (c) is a non-enzymatic detection method.

9. The method of claim 1, wherein said filter has a pore size between 0.1 and 1.5 μm.

10. The method of claim 1, wherein said colony is lifted from its growth media on the filter used in step (b).

11. The method of claim 10, wherein said colonies are lifted prior to the lysis of step (a).

12. The method of claim 1, wherein filtration step (b) includes the application of a force to the filter carrying the colonies.

13. The method of claim 1, wherein proteins in the filtrate from filtration step (b) are captured on a solid support prior to detection step (c)

14. The method of claim 1, wherein said protein is a membrane protein.

* * * * *

SEQUENCE LISTING

```
<160> NUMBER OF SEQ ID NOS: 1

<210> SEQ ID NO 1
<211> LENGTH: 18
<212> TYPE: DNA
<213> ORGANISM: prokaryotic or eukaryotic
<220> FEATURE:
<221> NAME/KEY: misc_feature
<222> LOCATION: (4)..(18)
<223> OTHER INFORMATION: n is a, c, g, or t

<400> SEQUENCE: 1
atgnnnnnnn nnnnnnnn                                                 18
```